US012674792B2

(12) United States Patent
Clark-Joseph

(10) Patent No.: US 12,674,792 B2
(45) Date of Patent: Jul. 7, 2026

(54) METHODS FOR VALIDATING MEDICATION

(71) Applicant: Valisure LLC, New Haven, CT (US)

(72) Inventor: Adam Clark-Joseph, Champaign, IL (US)

(73) Assignee: Valisure LLC, New Haven, CT (US)

( * ) Notice: Subject to any disclaimer, the term of this patent is extended or adjusted under 35 U.S.C. 154(b) by 0 days.

(21) Appl. No.: 19/411,089

(22) Filed: Dec. 5, 2025

(65) Prior Publication Data

US 2026/0092909 A1     Apr. 2, 2026

Related U.S. Application Data

(60) Division of application No. 19/327,963, filed on Sep. 12, 2025, which is a continuation of application No. 19/029,932, filed on Jan. 17, 2025, now abandoned, which is a continuation of application No. 18/732,336, filed on Jun. 3, 2024, now abandoned, which is a continuation of application No. 18/381,987, filed on Oct. 19, 2023, now abandoned, which is a continuation of application No. 18/111,314, filed on Feb. 17, 2023, now abandoned, which is a continuation of application No. 16/615,617, filed as application No.
(Continued)

(51) Int. Cl.
| | |
|---|---|
| *G01N 33/15* | (2006.01) |
| *G01N 21/25* | (2006.01) |
| *G01N 21/65* | (2006.01) |
| *G01N 24/08* | (2006.01) |
| *G06Q 30/018* | (2023.01) |
| *G16H 20/10* | (2018.01) |

(52) U.S. Cl.
CPC ............. *G01N 33/15* (2013.01); *G01N 21/25* (2013.01); *G01N 21/65* (2013.01); *G01N 24/08* (2013.01); *G06Q 30/018* (2013.01); *G16H 20/10* (2018.01)

(58) Field of Classification Search
CPC ........ G01N 33/15; G01N 21/25; G01N 21/65; G01N 24/08; G06Q 30/018; G16H 20/10
USPC ........................................................ 356/301
See application file for complete search history.

(56) References Cited

U.S. PATENT DOCUMENTS

| | | |
|---|---|---|
| 7,991,627 B2 | 8/2011 | Hutchinson et al. |
| 8,881,980 B2 | 11/2014 | Magill |
| | (Continued) | |

FOREIGN PATENT DOCUMENTS

| | | |
|---|---|---|
| CN | 105051740 A | 11/2015 |
| CN | 106204382 A | 12/2016 |
| | (Continued) | |

OTHER PUBLICATIONS

Co-pending U.S. Appl. No. 19/327,963, inventor Clark-Joseph; Adam, filed Sep. 12, 2025.
(Continued)

*Primary Examiner* — Md M Rahman
(74) *Attorney, Agent, or Firm* — WILSON SONSINI GOODRICH & ROSATI

(57) ABSTRACT

The present disclosure provides methods and systems for providing a validated drug product to an end-user or distributing business. Also provided herein are methods and systems for providing a certificate of analysis for a drug product to provide more information to a user.

11 Claims, 5 Drawing Sheets

Supply Chain Vulnerabilities

• Issues can be introduced anywhere along the chain

Related U.S. Application Data

PCT/US2018/033983 on May 22, 2018, now Pat. No. 11,619,619.

(60) Provisional application No. 62/509,592, filed on May 22, 2017.

(56) References Cited

U.S. PATENT DOCUMENTS

| | | | |
|---|---|---|---|
| 11,619,619 | B2 | 4/2023 | Clark-Joseph |
| 2005/0077476 | A1 | 4/2005 | Poteet et al. |
| 2005/0228594 | A1 | 10/2005 | Pryce-Lewis et al. |
| 2006/0160238 | A1 | 7/2006 | Lennernas |
| 2006/0287887 | A1 | 12/2006 | Hutchinson et al. |
| 2008/0319795 | A1 | 12/2008 | Poteet et al. |
| 2012/0278096 | A1 | 11/2012 | Holness |
| 2020/0312442 | A1* | 10/2020 | Hairr ...................... G16H 40/20 |
| 2021/0090699 | A1* | 3/2021 | Poirier ................... H04N 23/57 |
| 2021/0365849 | A1* | 11/2021 | Kamen .................. G16H 70/40 |

FOREIGN PATENT DOCUMENTS

| | | |
|---|---|---|
| WO | WO-2014120533 A1 | 8/2014 |
| WO | WO-2017156442 A1 | 9/2017 |
| WO | WO-2018217825 A1 | 11/2018 |

OTHER PUBLICATIONS

EP18805755.8 Extended European Search Report dated Jan. 20, 2021.

PCT/US2018/033983 International Search Report and Written Opinion dated Jul. 26, 2018.

U.S. Appl. No. 19/327,963 Corrected Notice of Allowability dated Jan. 29, 2026.

U.S. Appl. No. 19/327,963 Notice of Allowance dated Jan. 16, 2026.

U.S. Appl. No. 19/327,963 Office Action dated Dec. 11, 2025.

* cited by examiner

Figure 2

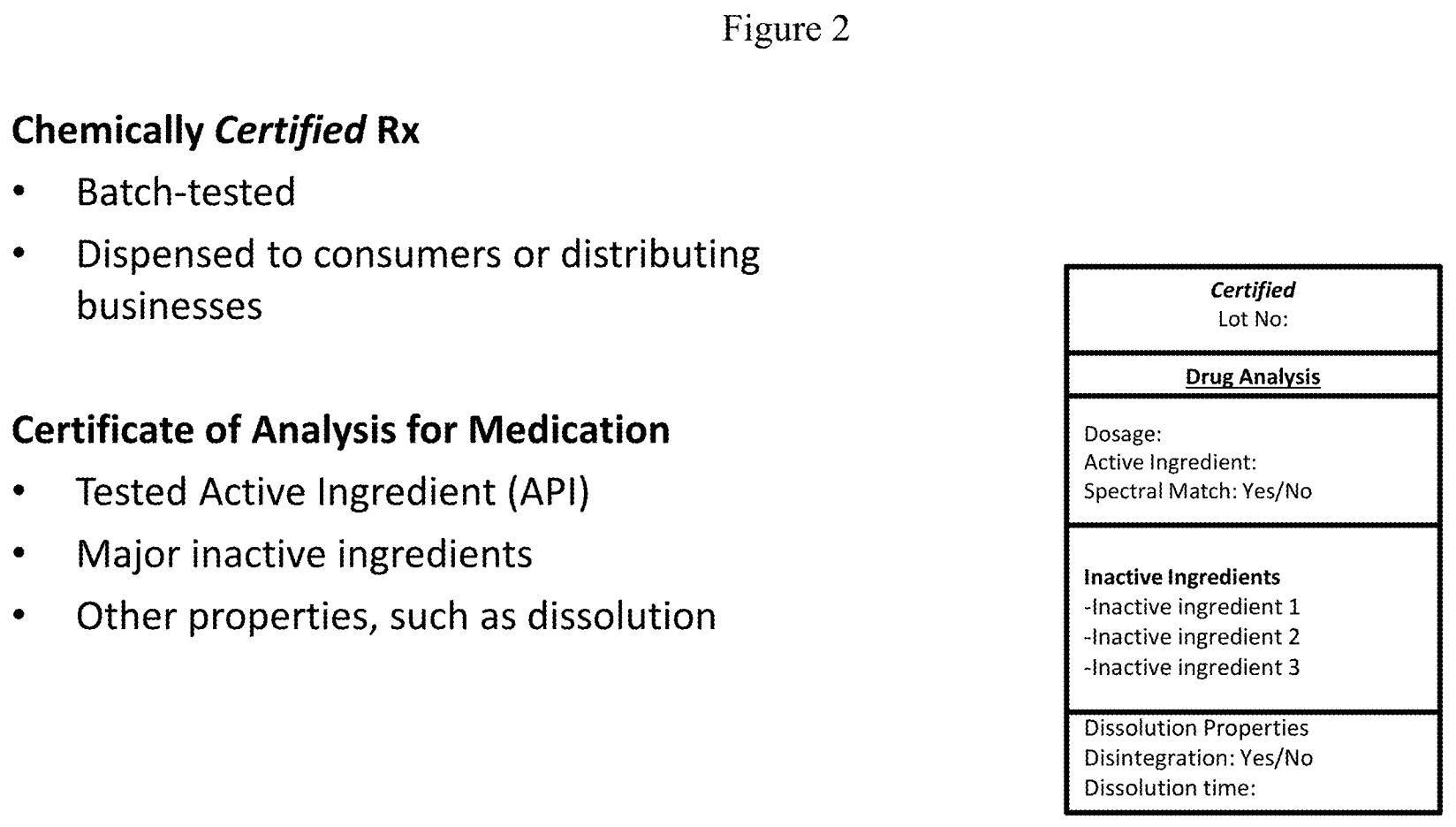

**Chemically *Certified* Rx**

- Batch-tested
- Dispensed to consumers or distributing businesses

Certificate of Analysis for Medication

- Tested Active Ingredient (API)
- Major inactive ingredients
- Other properties, such as dissolution

*Certified*
Lot No:

Drug Analysis

Dosage:
Active Ingredient:
Spectral Match: Yes/No

Inactive Ingredients
-Inactive ingredient 1
-Inactive ingredient 2
-Inactive ingredient 3

Dissolution Properties
Disintegration: Yes/No
Dissolution time:

Figure 4

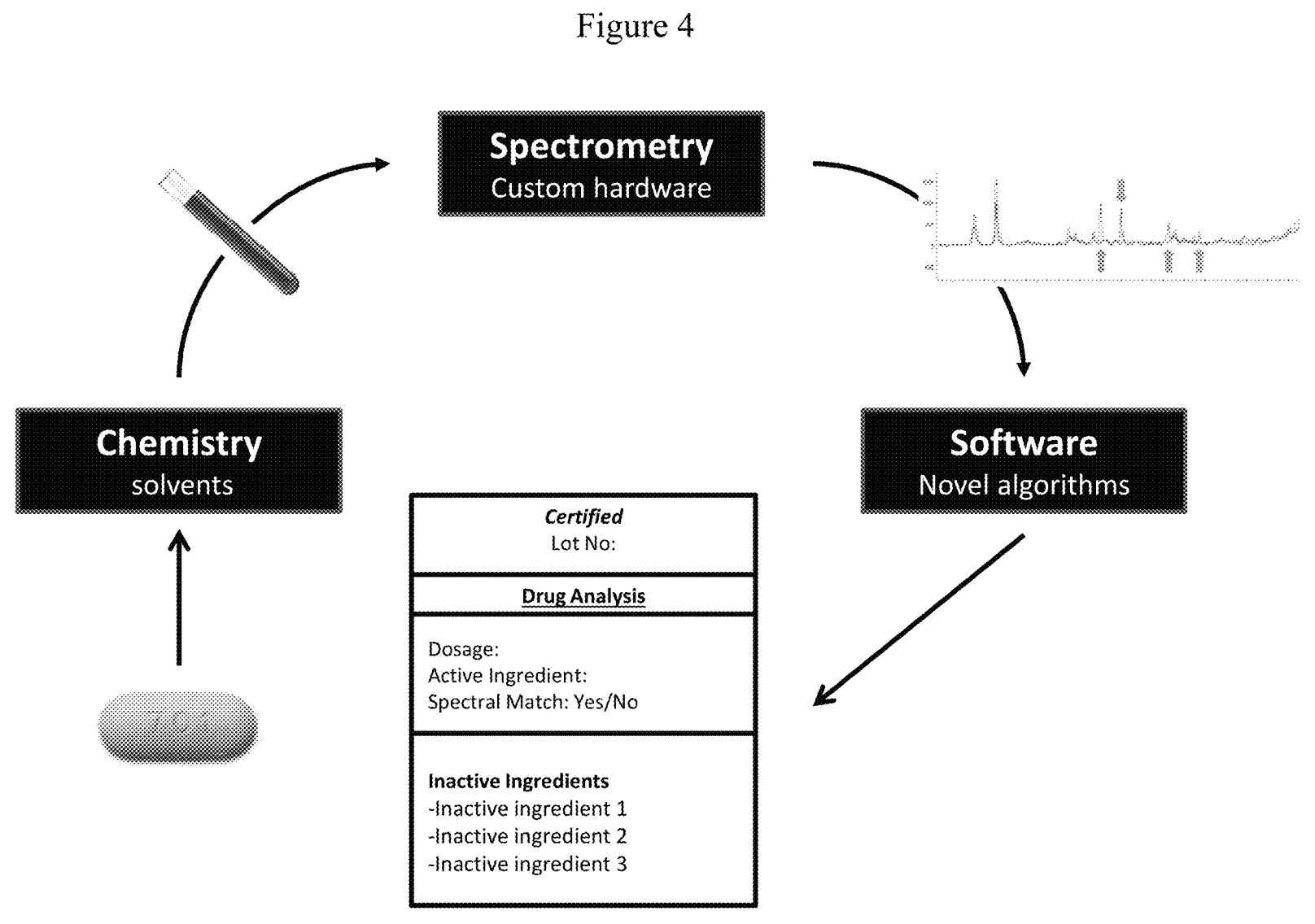

Spectrometry
Custom hardware

Software
Novel algorithms

Chemistry
solvents

Certified
Lot No:

Drug Analysis

Dosage:
Active Ingredient:
Spectral Match: Yes/No

Inactive Ingredients
-Inactive ingredient 1
-Inactive ingredient 2
-Inactive ingredient 3

METHODS FOR VALIDATING MEDICATION

CROSS-REFERENCE TO RELATED APPLICATIONS

This application is a divisional of U.S. patent application Ser. No. 19/327,963, filed Sep. 12, 2025, which is a continuation of U.S. patent application Ser. No. 19/029,932, filed Jan. 17, 2025, now abandoned, which is a continuation of U.S. patent application Ser. No. 18/732,336, filed Jun. 3, 2024, now abandoned, which is a continuation of U.S. patent application Ser. No. 18/381,987, filed Oct. 19, 2023, now abandoned, which is a continuation of U.S. patent application Ser. No. 18/111,314, filed Feb. 17, 2023, now abandoned, which is a continuation of U.S. patent application Ser. No. 16/615,617, filed Nov. 21, 2019, now U.S. Pat. No. 11,619,619, issued Apr. 4, 2023, which is a U.S. National Phase Application of International Patent Application No. PCT/US2018/033983, filed May 22, 2018, which claims the benefit of U.S. Provisional Application No. 62/509,592, filed May 22, 2017, each of which is herein incorporated by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

There is a considerable and increasing problem associated with counterfeit, impure, or substandard medications (e.g., pharmaceutical products) in both developing and developed countries. Accordingly, the ability to accurately identify, verify, and/or determine the composition, quantity, content, purity, and/or physical properties (such as dissolution rate) of medications is becoming an important issue not only for governments and corporations, but also for individuals and/or intended end-users of a product. For example, a lack of oversight for verifying identity, composition, and/or quantity of ingredients in pharmaceutical products can lead to unintended and adverse consequences for individual end-users.

Various types of non-analytical methods, such as matching end-user information with the prescription, are available to the end-user. However, analytical tests in order to identify and/or determine the chemical composition, quantity, content, purity and/or physical properties of medications such as drugs and biologics or other chemicals for validation may not be available to the end-user or other businesses in the pharmaceutical supply chain post-manufacturing. Current quality-control systems may rely on many different participants, with different incentives, at different stages of a long, complicated, decentralized supply chain to each perform separate, specific analyses; each link in the chain may assume that all previous testing earlier in the chain was performed and reported correctly, and that those test results remain valid regardless of conditions and events in the interim. If any of the testing, anywhere along this lengthy and complicated chain, is falsified, improperly performed, misreported, or otherwise compromised, the problem may propagate all the way through to the end. Because such issues have been found to arise frequently, verifying the mere provenance of a medication may not be an adequate verification of quality.

SUMMARY OF THE INVENTION

Recognizing a need for the ability to accurately identify, verify, and/or determine the composition, quantity, content, purity, and/or physical properties of medications such as drugs, the present disclosure provides methods and systems for analyzing ingredients of medications selected from a batch using analytical tests. Validated medications from the tested batch may then be provided to an end-user or distributing businesses based on meeting quality standards. Comprehensive, independent analysis is optionally performed close to the end or at the very end of the supply chain, optionally in the final step before medications are distributed to end-users or a distributing business; this penultimate quality control technique is an alternative to relying on a decentralized collection of test results reported by various parties at different stages of the supply chain.

In one aspect, provided herein are methods for analyzing a unit of a medication in order to determine a validation status of a medication batch. A batch of medication may be the whole batch produced at a manufacturer or a subset of batch that has been split off from the original batch. The method comprises: receiving the unit of the medication, wherein the unit of the medication is from the medication batch or subset of a batch; analyzing an ingredient of the unit of the medication using an analytical test thereby generating an analysis result; comparing the analysis result to a reference or derivative thereof thereby generating a comparison result; determining the validation status of the medication batch or subset of a batch based on the comparison result; and providing a validated unit of the medication to an end-user or distributing business, wherein the validated unit of the medication is from the medication batch or subset of a batch.

In some embodiments, if analysis of a batch reveals that the batch fails to meet validation criteria, units from that batch are not dispensed. In some embodiments, the end-user is an individual for which the medication was prescribed. In some embodiments, the distributing business is a hospital, wholesaler, or distributor. In some embodiments an analytical test is performed using a nuclear magnetic resonance spectroscopy, mass spectrometry, high-performance liquid chromatography, Fourier transform infrared spectroscopy or Raman spectroscopy. In some embodiments, an analytical test is performed using Raman spectroscopy. In some embodiments, an analytical test comprises a plurality of analytical tests. In some embodiments, an ingredient comprises an active pharmaceutical ingredient. In some embodiments, an ingredient comprises an inactive ingredient. In some embodiments, a reference or a derivative thereof comprises a reference composition of a reference unit of a medication, a reference concentration of an ingredient, a reference quantity of an ingredient or a combination thereof. In some embodiments, a reference or a derivative thereof comprises a reference composition of a reference unit of a medication. In some embodiments, a reference composition of a reference unit of a medication comprises an ingredient. In some embodiments, analyzing comprises determining a composition of a unit of a medication. In some embodiments, a validated unit of a medication is provided to an end-user or distributing business if at least 80%, 85%, 90%, 95%, 97%, 98%, 99%, or 99.5% of a composition of a unit of a medication corresponds to a reference composition. In some embodiments, a reference or a derivative thereof comprises a reference concentration of the ingredient. In some embodiments, analyzing comprises measuring a concentration of an ingredient in a medication. In some embodiments, a validated unit of a medication is provided to an end-user or distributing business if a concentration of an ingredient is within 10%, 5%, 3%, 2%, or 1% of a reference concentration of the ingredient. In some embodiments, a validated unit of a medication is provided to an end-user if a concentration of an ingredient is within 10%, 5%, 3%, 2%, or 1% of reference concentration of the ingredient. In some embodiments, a reference or a derivative thereof comprises a reference quantity of an ingredient. In some embodiments, analyzing comprises measuring a quantity of an ingredient in the medication. In some embodiments, validated unit of a medication is provided to the end-user or distributing business if a quantity of the ingredient is within 5% of a reference quantity of the ingredient. In some embodiments, a validated unit of a medication is provided to the end-user or distributing business if the quantity of the ingredient is within 3% of a reference quantity of the ingredient. In some embodiments, validation of a validated unit of a medication is indicated by a certificate of analysis. In some embodiments, a certificate of analysis comprises a number of analytical tests performed on a unit of medication, a number of ingredients analyzed, deviation from a reference concentration, deviation from a reference quantity and/or dissolution test results. In some embodiments, a certificate of analysis is an electronic certificate of analysis. In some embodiments, a certificate of analysis is a physical certificate of analysis. In some embodiments, a medication batch or subset of a batch comprises at least 100, 500, 1,000, 5,000, 10,000, 20,000, 50,000, 100,000, 200,000, 500,000, 1,000,000, 2,000,000, 5,000,000, 10,000,000 or more units of the medication. In some embodiments, a validated unit of a medication is categorized based on (a) a composition of a validated unit of a medication; (b) a concentration of an ingredient relative to a reference or a derivative thereof; (c) a quantity of an ingredient relative to a reference or a derivative thereof; (d) a number of analytical tests performed. In some embodiments, a portion of a unit of a medication is dissolved in a solvent.

In another aspect, the present disclosure provides a method comprising: (a) analyzing an ingredient of a medication using an analytical test, wherein the medication is from a medication batch or subset of a batch; (b) comparing the ingredient to a reference or derivative thereof; and (c) providing a validated medication to an end-user or distributing business, wherein the validated medication is from the medication batch or subset of a batch.

In some embodiments, the end-user is an individual for which the medication was prescribed. In some embodiments, the distributing business is a hospital, wholesaler, or distributor. In some embodiments an analytical test is performed using a nuclear magnetic resonance spectroscopy, mass spectrometry, high-performance liquid chromatography, Fourier transform infrared spectroscopy or Raman spectroscopy. In some embodiments, an analytical test is performed using Raman spectroscopy. In some embodiments, an analytical test comprises a plurality of analytical tests. In some embodiments, an ingredient comprises an active pharmaceutical ingredient. In some embodiments, an ingredient comprises an inactive ingredient. In some embodiments, a reference or a derivative thereof comprises a reference composition of a reference unit of a medication, a reference concentration of an ingredient, a reference quantity of an ingredient or a combination thereof. In some embodiments, a reference or a derivative thereof comprises a reference composition of a reference unit of a medication. In some embodiments, a reference composition of a reference unit of a medication comprises an ingredient. In some embodiments, analyzing comprises determining a composition of a unit of a medication. In some embodiments, a validated unit of a medication is provided to an end-user or distributing business if at least 80%, 85%, 90%, 95%, 97%, 98%, 99%, or 99.5% of a composition of a unit of a medication corresponds to a reference composition. In some embodiments, a reference or a derivative thereof comprises a reference concentration of the ingredient. In some embodiments, analyzing comprises measuring a concentration of an ingredient in a medication. In some embodiments, a validated unit of a medication is provided to an end-user or distributing business if a concentration of an ingredient is within 10%, 5%, 3%, 2%, or 1% of a reference concentration of the ingredient. In some embodiments, a validated unit of a medication is provided to an end-user if a concentration of an ingredient is within 10%, 5%, 3%, 2%, or 1% of reference concentration of the ingredient. In some embodiments, a reference or a derivative thereof comprises a reference quantity of an ingredient. In some embodiments, analyzing comprises measuring a quantity of an ingredient in the medication. In some embodiments, validated unit of a medication is provided to the end-user or distributing business if a quantity of the ingredient is within 5% of a reference quantity of the ingredient. In some embodiments, a validated unit of a medication is provided to the end-user or distributing business if the quantity of the ingredient is within 3% of a reference quantity of the ingredient. In some embodiments, validation of a validated unit of a medication is indicated by a certificate of analysis. In some embodiments, a certificate of analysis comprises a number of analytical tests performed on a unit of medication, a number of ingredients analyzed, deviation from a reference concentration, deviation from a reference quantity and/or dissolution test results. In some embodiments, a certificate of analysis is an electronic certificate of analysis. In some embodiments, a certificate of analysis is a physical certificate of analysis. In some embodiments, a medication batch or subset of a batch comprises at least 100, 500, 1,000, 5,000, 10,000, 20,000, 50,000, 100,000, 200,000, 500,000, 1,000,000, 2,000,000, 5,000,000, 10,000,000 or more units of the medication. In some embodiments, a validated unit of a medication is categorized based on (a) a composition of a validated unit of a medication; (b) a concentration of an ingredient relative to a reference or a derivative thereof; (c) a quantity of an ingredient relative to a reference or a derivative thereof; (d) a number of analytical tests performed. In some embodiments, a portion of a unit of a medication is dissolved in a solvent.

In another aspect, provided herein are systems for providing a validated unit of a medication to an end-user or distributing business, comprising: one or more processors; and a non-transitory computer readable medium comprising instructions operable, when executed by the one or more processors, to cause the system to: receive, over a communication network, a prescription for the medication or an order for a medication product or consumable not requiring a prescription; analyze an ingredient of the unit of the medication using an analytical test thereby generating an analysis result; comparing the analysis result to a reference or derivative thereof thereby generating a comparison result; determining a validation status of the medication batch based on the comparison result; and providing the validated unit of the medication to the end-user or distributing business, wherein the validated unit of the medication is from the medication batch or subset of a batch.

In some embodiments, the end-user is an individual for which the medication was prescribed. In some embodiments, the distributing business is a hospital, wholesaler, or distributor. In some embodiments an analytical test is performed using a nuclear magnetic resonance spectroscopy, mass spectrometry, high-performance liquid chromatography, Fourier transform infrared spectroscopy or Raman spectroscopy. In some embodiments, an analytical test is performed using Raman spectroscopy. In some embodiments, an analytical test comprises a plurality of analytical tests. In some embodiments, an ingredient comprises an active pharmaceutical ingredient. In some embodiments, an ingredient comprises an inactive ingredient. In some embodiments, a reference or a derivative thereof comprises a reference composition of a reference unit of a medication, a reference concentration of an ingredient, a reference quantity of an ingredient or a combination thereof. In some embodiments, a reference or a derivative thereof comprises a reference composition of a reference unit of a medication. In some embodiments, a reference composition of a reference unit of a medication comprises an ingredient. In some embodiments, analyzing comprises determining a composition of a unit of a medication. In some embodiments, a validated unit of a medication is provided to an end-user or distributing business if at least 80%, 85%, 90%, 95%, 97%, 98%, 99%, or 99.5% of a composition of a unit of a medication corresponds to a reference composition. In some embodiments, a reference or a derivative thereof comprises a reference concentration of the ingredient. In some embodiments, analyzing comprises measuring a concentration of an ingredient in a medication. In some embodiments, a validated unit of a medication is provided to an end-user or distributing business if a concentration of an ingredient is within 10%, 5%, 3%, 2%, or 1% of a reference concentration of the ingredient. In some embodiments, a validated unit of a medication is provided to an end-user if a concentration of an ingredient is within 10%, 5%, 3%, 2%, or 1% of reference concentration of the ingredient. In some embodiments, a reference or a derivative thereof comprises a reference quantity of an ingredient. In some embodiments, analyzing comprises measuring a quantity of an ingredient in the medication. In some embodiments, validated unit of a medication is provided to the end-user or distributing business if a quantity of the ingredient is within 5% of a reference quantity of the ingredient. In some embodiments, a validated unit of a medication is provided to the end-user or distributing business if the quantity of the ingredient is within 3% of a reference quantity of the ingredient. In some embodiments, validation of a validated unit of a medication is indicated by a certificate of analysis. In some embodiments, a certificate of analysis comprises a number of analytical tests performed on a unit of medication, a number of ingredients analyzed, deviation from a reference concentration, deviation from a reference quantity and/or dissolution test results. In some embodiments, a certificate of analysis is an electronic certificate of analysis. In some embodiments, a certificate of analysis is a physical certificate of analysis. In some embodiments, a medication batch or subset of a batch comprises at least 100, 500, 1,000, 5,000, 10,000, 20,000, 50,000, 100,000, 200,000, 500,000, 1,000,000, 2,000,000, 5,000,000, 10,000,000 or more units of the medication. In some embodiments, a validated unit of a medication is categorized based on (a) a composition of a validated unit of a medication; (b) a concentration of an ingredient relative to a reference or a derivative thereof; (c)

a quantity of an ingredient relative to a reference or a derivative thereof; (d) a number of analytical tests performed. In some embodiments, a portion of a unit of a medication is dissolved in a solvent.

In another aspect, the present disclosure provides a system for obtaining a validated medication by an end-user or distributing business, comprising: a computer, in communication with the communication interface, wherein the computer comprises one or more computer processors and a computer readable medium comprising machine-executable code that, upon execution by the one or more computer processors, implements a method comprising: (a) receiving, over the communication network, a prescription for a medication from a physician, or an order for a non-prescription medication or medication-like product, wherein the medication is obtained and analyzed for an ingredient in the medication using an analytical test, wherein the medication is from a medication batch or subset of a batch; and (b) comparing the ingredient to a reference or derivative thereof; and (c) providing the a validated medication to the end-user or distributing business, wherein the validated medication is from the medication batch or subset of a batch.

In another aspect, the present disclosure provides a system for validating a medication, comprising: (a) an instrument for analyzing an ingredient of a medication in an analytical test, wherein the medication is from a medication batch or subset of a batch; and (b) a computer, in communication with the communication interface, wherein the computer comprises one or more computer processors and a computer readable medium comprising machine-executable code that, upon execution by the one or more computer processors, implements a method comprising: (i) receiving, over the communication network, a prescription for the medication from a physician or an order for a non-prescription medication or medication-like product for analyzing the ingredient using the instrument in (a); (ii) comparing the ingredient to a reference or derivative thereof; and (ii) providing a validated medication to an end-user or distributing business.

In some embodiments, the end-user is an individual for which the medication was prescribed. In some embodiments, the distributing business is a hospital, wholesaler, or distributor. In some embodiments an analytical test is performed using a nuclear magnetic resonance spectroscopy, mass spectrometry, high-performance liquid chromatography, Fourier transform infrared spectroscopy or Raman spectroscopy. In some embodiments, an analytical test is performed using Raman spectroscopy. In some embodiments, an analytical test comprises a plurality of analytical tests. In some embodiments, an ingredient comprises an active pharmaceutical ingredient. In some embodiments, an ingredient comprises an inactive ingredient. In some embodiments, a reference or a derivative thereof comprises a reference composition of a reference unit of a medication, a reference concentration of an ingredient, a reference quantity of an ingredient or a combination thereof. In some embodiments, a reference or a derivative thereof comprises a reference composition of a reference unit of a medication. In some embodiments, a reference composition of a reference unit of a medication comprises an ingredient. In some embodiments, analyzing comprises determining a composition of a unit of a medication. In some embodiments, a validated unit of a medication is provided to an end-user or distributing business if at least 80%, 85%, 90%, 95%, 97%, 98%, 99%, or 99.5% of a composition of a unit of a medication corresponds to a reference composition. In some embodiments, a reference or a derivative thereof comprises a reference concentration of the ingredient. In some embodiments, analyzing comprises measuring a concentration of an ingredient in a medication. In some embodiments, a validated unit of a medication is provided to an end-user or distributing business if a concentration of an ingredient is within 10%, 5%, 3%, 2%, or 1% of a reference concentration of the ingredient. In some embodiments, a validated unit of a medication is provided to an end-user if a concentration of an ingredient is within 10%, 5%, 3%, 2%, or 1% of reference concentration of the ingredient. In some embodiments, a reference or a derivative thereof comprises a reference quantity of an ingredient. In some embodiments, analyzing comprises measuring a quantity of an ingredient in the medication. In some embodiments, validated unit of a medication is provided to the end-user or distributing business if a quantity of the ingredient is within 5% of a reference quantity of the ingredient. In some embodiments, a validated unit of a medication is provided to the end-user or distributing business if the quantity of the ingredient is within 3% of a reference quantity of the ingredient. In some embodiments, validation of a validated unit of a medication is indicated by a certificate of analysis. In some embodiments, a certificate of analysis comprises a number of analytical tests performed on a unit of medication, a number of ingredients analyzed, deviation from a reference concentration, deviation from a reference quantity and/or dissolution test results. In some embodiments, a certificate of analysis is an electronic certificate of analysis. In some embodiments, a certificate of analysis is a physical certificate of analysis. In some embodiments, a medication batch or subset of a batch comprises at least 100, 500, 1,000, 5,000, 10,000, 20,000, 50,000, 100,000, 200,000, 500,000, 1,000,000, 2,000,000, 5,000,000, 10,000,000 or more units of the medication. In some embodiments, a validated unit of a medication is categorized based on (a) a composition of a validated unit of a medication; (b) a concentration of an ingredient relative to a reference or a derivative thereof; (c) a quantity of an ingredient relative to a reference or a derivative thereof; (d) a number of analytical tests performed. In some embodiments, a portion of a unit of a medication is dissolved in a solvent.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 illustrates an exemplary embodiment of dispensing prescription medication, in accordance with embodiments.

FIG. 4 illustrates an exemplary medication distribution model, in accordance with embodiments.

DETAILED DESCRIPTION

Overview

Figure 1:
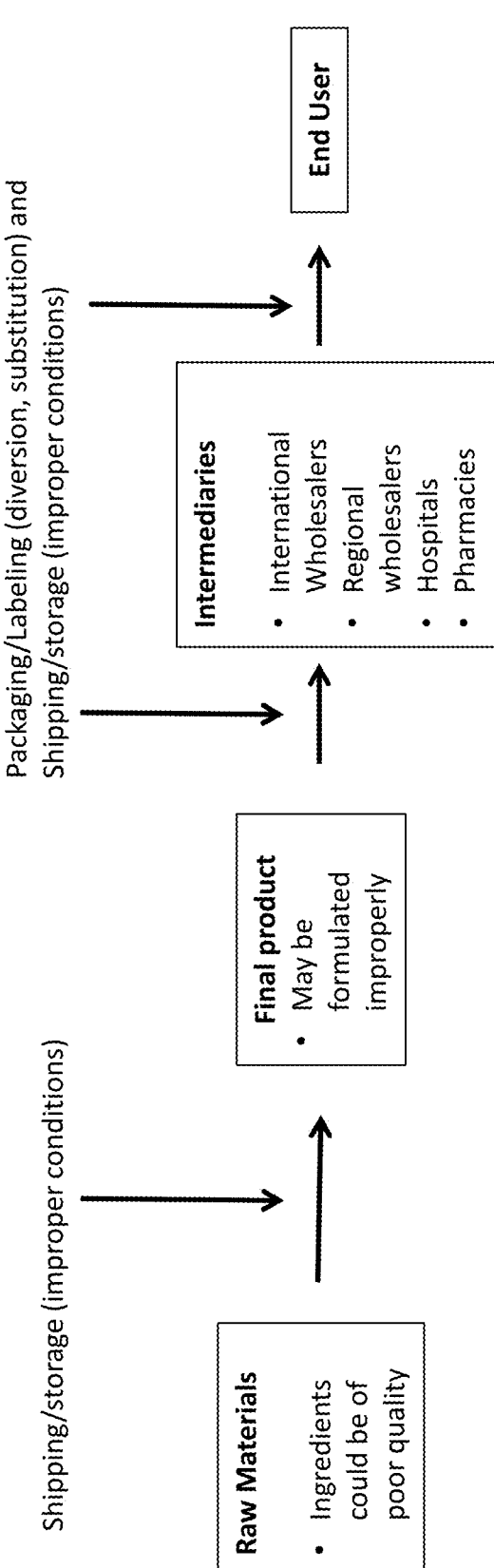
FIG. 1 illustrates exemplary supply chain vulnerabilities that may affect variability of medication, in accordance with embodiments.

The present disclosure provides methods and systems for validating medication for an end-user or distributing business. In the context of samples comprising active ingredients, counterfeit and substandard medications may be a considerable and ever growing problem, both in developing and developed economies. For example, for end-users or distributing businesses of samples (e.g., drugs, biologics, etc), there may be little or no oversight in ensuring that the appropriate ingredients (e.g., both active and inactive ingredients) are incorporated in the correct specified proportions in the sample, or that an appropriate amount of the active ingredient is present, oftentimes leading to improper dosing for the user. In some instances, improper excipients in the sample may lead to undesirable and adverse reactions in the user. In some instances, improper dissolution or disintegration properties may produce adverse clinical outcomes.

The present disclosure may provide methods for verifying medication or providing assurance regarding a quality of the medication, such that an entity employing the methods can ensure every batch of medication the entity distributes or dispenses satisfies established quality standards, as determined by integrated chemical analyses performed toward the end-stage of the supply-chain, immediately before the medication is distributed or dispensed. The entity may only distribute/dispense from batches of drugs for which the batch meets the stipulated criteria. For example, if analysis of a batch reveals that the batch fails to meet validation criteria, units from that batch are not dispensed or distributed. Various aspects of the present disclosure may be applied to any of the particular applications set forth below or for any other types of drugs, medications, supplements, consumables, etc.

While the term medication or drug may be used primarily herein, it is to be understood that these terms may encompass any consumable comprising an active ingredient or ingredient of interest. The ingredient of interest may be an active ingredient, such as an active pharmaceutical ingredient. It shall be understood that different aspects of the present disclosure can be appreciated individually, collectively, or in combination with each other.

The methods and systems of the present disclosure provide a means for determining one or more characteristics of a medication. In some cases, a single characteristic may be determined for validating a medication. In some cases, more than one characteristic may be determined. In some instances, a characteristic may comprise quantities of ingredients (e.g. active pharmaceutical ingredient, active substances, active constituent, proteins, etc) and/or excipients. In some examples, a characteristic may comprise composition of the medication. In some examples, a characteristic may comprise dissolution properties of the medication. In some other examples, a characteristic may comprise concentrations of ingredients. In some aspects, the one or more characteristics may include the identity and/or quantity of more than one ingredient in the sample. For example, the methods may identify 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 different ingredients in the sample. In some cases, the methods may identify one or more characteristics of the more than one ingredient substantially simultaneously. In some aspects, the one or more characteristics may include the identity and/or quantity of more than one excipient in the sample. For example, the methods may identify 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more than 50 different excipients in the sample. In some cases, the methods may identify one or more characteristics of the more than one excipient substantially simultaneously.

The characteristics of the sample or unit may be determined without regards to a physical form (e.g., size, shape, etc.) of the sample. For example, the methods and systems of the present disclosure may be utilized to determine characteristics of the sample without having to be calibrated differently depending on the physical form of the sample. In some instances, calibrating for an active ingredient sample may allow the methods, devices, and systems described herein to be utilized for differing samples (e.g. differing in physical forms) but comprising a same active ingredient. Optionally, processing the samples into a solution comprising the ingredient with aid of appropriate solvents may facilitate this process.

Compositions

As described herein, samples may comprise both active ingredients, also referred to as ingredients of interest, and/or other components such as inactive ingredients or excipients. The active ingredients may refer to biologically active components in the samples. The active ingredient may confer bio-activity or pharmacological activity to the sample, and may confer therapeutic effect to the samples in some instances.

Excipients may refer to substances other than the active ingredients which are included in the manufacturing process or are contained in a finished sample dosage form. Excipients may include, but are not limited to, diluents, fillers, binders, disintegrants, lubricants, coloring agents, and preservatives. Even if inactive, the excipients may in some instances significantly affect chemical and/or physical properties of the sample and its biopharmaceutical profile. For some samples, the excipients may make up the bulk of the total dosage form.

In some instances, the excipients may play an important function for the sample in various aspects. For example, the excipients may play part in the manufacturing process of the sample; the excipients may be important for keeping the active ingredient from being released too early in the assimilation process in places where it could damage tender tissue and create gastric irritation or stomach upsets; the excipients may help the sample disintegrate into particles small enough to reach the blood stream more quickly; the excipients may protect the sample's stability so it will be at maximum effectiveness at time of use; the excipients may be used to aid the identification of the sample; the excipients may be used simply to make the sample taste and look better.

The methods and systems provided herein allow for the analysis of small quantities of samples or units of medications such as pills, tablets, capsules, etc. Samples and units of medications can be used interchangeably herein. For example, the present disclosure provides the means for analyzing individual samples. The samples may be received from an end user or by an individual or entity that supplies the sample directly to an end user. Accordingly, the present disclosure provides a means for individuals to get analysis done for samples (e.g., drugs, medications, biologics, etc) they may be taking. The analysis may provide information regarding both active ingredients and/or inactive ingredients. For example, the analysis may help determine an identity of the active ingredients and/or the inactive ingredients. In some instances, the analysis may help quantify an amount of the active ingredients and/or the inactive ingredients.

Advantageously, certain properties of the methods and systems (e.g., ability to provide analysis for individual samples or pills, ability to provide analysis to samples of differing physical sizes or shapes without having to recalibrate for the differing sizes and shapes, etc) may enable the servicing of individual end-users of samples for the analysis of the samples (e.g., batch of samples).

For example, a pharmacy may receive a batch of prescription drugs but may be uncertain that it contains the appropriate active ingredients, or an appropriate amount of the active ingredient. In some instances, the pharmacy may be cautious of whether the drug contains inappropriate excipients. The pharmacy may send in one or more drugs of the batch, and the disclosure provided herein may provide a means for the determining the characteristics of the drug, e.g., identities and/or quantities of the active ingredients and/or excipients. After receiving a report, or result of the analysis, the pharmacy may be reassured that the sample is as expected, or informed that the sample is substandard.

Analysis

In certain aspects, methods and systems are provided for the analysis of a sample. In some cases, the methods, devices, and systems can be used to determine one or more characteristics of a sample, including an identity, composition, or quantity of components within the sample. The components may include active ingredients and/or excipients. The methods, devices, and systems may overcome the various shortcomings experienced by existing technologies. For example, the systems may have low instrument cost, utilize consumables with low cost, provide quick and accurate analysis, be capable of accomplishing analyses of mixtures, be capable of analyzing low concentrations, be capable of analyzing or identifying a unique chemical ID, be capable of identifying solids, and not require expertise or special technical training for operation. In addition, the systems may be capable of analyzing a plurality of different samples having differing sizes, shapes, density, etc without having a need for separate calibration. In some instances, the systems may be capable of analyzing a plurality of different samples if the samples have a same ingredient of interest, e.g. active pharmaceutical ingredient. In some instances, the system may be capable of universally analyzing samples having a same ingredient of interest, e.g. without calibrations specific to the different samples. In some instances, the system may be capable of universally analyzing samples having a same ingredient of interest, e.g. without calibration in between the different samples.

As described throughout, the calibrating step may be performed once for a given ingredient (e.g. API) and it may not be necessary to perform a new calibration process for different samples that contain the same ingredient. For example a sample may comprise a same ingredient but may comprise differing compositions, sizes, weights, shapes, excipients, etc. Nevertheless the devices and systems provided herein may be universally applicable for the different samples (e.g. processed samples) after the initial calibration step that calibrates for the given ingredient. As an example, a calibration that is performed for acetaminophen in a given solvent may be applied to oblong 500 mg acetaminophen pills from manufacturer A, round 100 mg acetaminophen pills from manufacturer B, and so on. As another example, a calibration that is performed for acetaminophen in a given solvent may be applied to oblong 500 mg acetaminophen pills from manufacturer A, round 100 mg acetaminophen pills from manufacturer B, and so on, even if the inactive ingredients in those pills are different.

Calibration

In some instances, the calibrating step may comprise selecting pairs of locations (i.e., wave-numbers) at which the ratio of spectral intensities is compared. While a single pair may be utilized for the calibrating step, a plurality of different pairs may be utilized in some instances. In some instances, using a plurality of different pairs may enable a more accurate and robust determination of the characteristics of the ingredients. In some instances, the pairs of locations may be tailored so as to avoid regions where there may be interference that may interfere with determination of characteristics of the ingredient. In some instances, the optimal pairs of locations may be selected autonomously, with the aid of one or more processors.

In some instances, the calibrating step may utilize a database. In some instances, the database may comprise information regarding a known ingredient (e.g. API) for a particular sample and excipients within the particular sample. In some instances, the information from the database may be utilized to determine possible or relevant excipients that may be encountered when analyzing a sample (e.g. pill) containing a given ingredient (e.g. API). In some instances, a spectra of excipients dissolved in the solvents may be measured or recorded, and spectral features of the excipients'spectra may be determined. Subsequently, when selecting for the optimal spectral location-pairs to use in the calibration, those locations that lie in regions where relevant excipients are found to have spectral activity may be avoided in being selected.

The methods and systems can be used to analyze a sample to be provided to an end-user or distributing business. The methods and systems can be used to analyze a sample to be provided to an end-user or distributing business immediately following analysis.

End User and Samples

In certain aspects, a sample containing an ingredient is obtained. The sample can be provided by an individual or an entity, including the entity that may eventually distribute medications from the batch from which the sample was taken. The entity or individual may be an entity or individual who will dispense the sample to an end user. The individual can be a medical professional. The individual can be a pharmacist or an employee of a pharmacy, analytical laboratory or medical profession. The individual may be, for example, an end-user of a product from which the sample is obtained. The end-user may refer to a potential user of the product. In some instances, the end-user may be an intended user of the product. In some instances, the end-user may refer to a purchaser of the product. For example, the end-user may be a patient who gets prescribed prescription drugs. For example, the end-user may be a consumer who purchases an over the-counter-drug or supplement. The term "product" as used herein may refer, in some cases, to a source of the sample (e.g., the sample is a portion of the product or is obtained from the product), or the terms "sample" and "product" may be used interchangeably and may refer to the same entity. The sample may be in a liquid state, a solid state, or a semi-solid state, such as a gel, cream, or paste. In some instances, the sample is a drug. Alternatively or in addition, the sample is a biologic, biopharmaceutical, supplement, or veterinary drug. In some cases, the sample is a pharmaceutical sample. In some cases, the pharmaceutical sample is in a solid form, non-limiting examples including, pills, tablets, capsules, powders and the like. In some cases, the pharmaceutical sample is a drug prescribed by a licensed healthcare practitioner. In other cases, the pharmaceutical sample is a drug purchased over-the-counter, for example, at a drug store. In some cases, the pharmaceutical sample is a drug purchased e.g. over the Internet. In some cases, the pharmaceutical sample is a drug purchased from a distributor or manufacturer. In some cases, an end-user of a product from which the pharmaceutical sample is obtained is desirous of verifying or confirming the composition of the product. In some cases, an end-user can validate a sample or a unit of a medication taken from a container or package containing more than one unit of the medication. In some instance, an end-user can validate a single pill in a pill bottle to determine the composition or safety of the contents of a pill bottle (the remaining medication in the pill bottle).

For example, a composition of a sample may be verified or validated. As another example, an amount of an ingredient of interest in the sample may be quantified. Techniques disclosed herein may be performed by any known analytical tests (e.g., by performing a plurality of analytical tests for a plurality of quality metrics). Non-limiting examples of techniques (analytical test) for identifying chemicals and verifying the integrity of pharmaceutical products may include, for example, nuclear magnetic resonance spectroscopy (NMR), mass spectrometry (MS), high-performance liquid chromatography (HPLC), Fourier transform infrared (FT-IR) spectroscopy and Raman spectroscopy. In some examples, Raman spectroscopy may be utilized to analyze the quantity or composition of a sample (e.g., a pill, tablet, capsule, etc). In some cases, the methods, devices, and systems may provide improvements to existing technologies. For example, the time from sample to answer may be substantially faster than traditional methods. Optionally, the methods, devices, and systems may provide more accurate quantifications than traditional methods. In some cases, the methods may be cheaper to perform than traditional methods and may not require expertise or special technical training for operation.

In some cases, the sample contains one or more ingredients. Ingredients may be active ingredients or inactive ingredients. In some instances, the active ingredients may be biologically or chemically active ingredients. In some cases, the sample is a pharmaceutical sample and contains one or more active pharmaceutical ingredients (API). The terms "active pharmaceutical ingredients" or "API" may refer to an ingredient that is biologically active. In some cases, the pharmaceutical sample contains one API. In some cases, the pharmaceutical sample contains more than one API. In some aspects, the methods, devices, and systems provided herein are utilized to determine one or more characteristics of one or more APIs contained within a sample. Any API can be interrogated utilizing the methods, devices, and systems provided herein.

Non-limiting examples of APIs suitable for interrogation with the methods, devices, and systems described herein may include; Hydrocodone/APAP (Brand Name: Vicodin®); Amoxicillin (Brand Name: Amoxil®); Lisinopril (Brand Name: Prinivil®); Esomeprazole (Brand Name: Nexium®); Atorvastatin (Brand Name: Lipitor®); Simvastatin (Brand Name: Zocor®); Clopidogrel (Brand Name: Plavix®); Montelukast (Brand Name: Singulair®); Rosuvastatin (Brand Name: Crestor®); Metoprolol (Brand Name: Lopressor®); Escitalopram (Brand Name: Lexapro®); Azithromycin (Brand Name: Zithromax®); Albuterol (Brand Name: ProAir® HFA); Hydrochlorothiazide (Brand Name: HCTZ); Metformin (Brand Name: Glucophage®); Sertraline (Brand Name: Zoloft®); Ibuprofen (Brand Name: Advil®); Zolpidem (Brand Name: Ambien®); Furosemide (Brand Name: Lasix®); Omeprazole (Brand Name: Prilosec®); Trazodone (Brand Name: Desyrel®); Valsartan (Brand Name: Diovan®); Tramadol (Ultram®); Duloxetine (Brand Name: Cymbalta®); Warfarin (Brand Name: Coumadin®); Amlodipine (Brand Name: Norvasc®); Oxyco-done/APAP (Brand Name: Percocet®); Quetiapine (Brand Name: Seroquel®); Promethazine (Brand Name: Phener-gan®); Fluticasone (Brand Name: Flonase®); Alprazolam (Brand Name: Xanax®); Clonazepam (Brand Name: Klo-nopin®); Benazepril (Brand Name: Lotensin®); Meloxicam (Brand Name: Mobic®); Citalopram (Brand Name: Cel-exa®); Cephalexin (Brand Name: Keflex®); Tiotropium (Brand Name: Spiriva®); Gabapentin (Brand Name: Neu-rontin®); Aripiprazole (Brand Name: Abilify®); Cycloben-zaprine (Brand Name: Flexeril®); Methylprednisolone (Brand Name: Medrol®); Methylphenidate (Brand Name: Ritalin®); Fexofenadine (Brand Name: Allegra®); Carvedilol (Brand Name: Coreg®); Carisoprodol (Brand Name: Soma®); Digoxin (Brand Name: Lanoxin®); Memantine (Brand Name: Namenda®); Atenolol (Brand Name: Tenormin®); Diazepam (Brand Name: Valium®); Oxycodone (Brand Name: OxyContin®); Risedronate (Brand Name: Actonel®); Folic Acid (Brand Name: Folvite®); Olmesartan (Brand Name: Benicar®); Predni-sone (Brand Name: Deltasone®); Doxycycline (Brand Name: Vibramycin®); Alendronate (Brand Name: Fosa-max®); Pantoprazole (Brand Name: Protonix®); Tamsu-losin (Brand Name: Flomax®); Triamterene/HCTZ (Brand Name: Dyazide®); Paroxetine (Brand Name: Paxil®); Buprenorphine (Brand Name: Suboxone®); Enalapril (Brand Name: Vasotec®); Lovastatin (Brand Name: Meva-cor®); Pioglitazone (Brand Name: Actos®); Pravastatin (Brand Name: Pravachol®); Fluoxetine (Brand Name: Pro-zac®); Insulin Detemir (Brand Name: Levemir®); Flucona-zole (Brand Name: Diflucan®); Levofloxacin (Brand Name: Levaquin®); Rivaroxaban (Brand Name: Xarelto®); Cele-coxib (Brand Name: Celebrex®); Codeine/APAP (Brand Name: Tylenol® #2); Mometasone (Brand Name: Nasonex®); Ciprofloxacin (Brand Name: Cipro®); Insulin Aspart (Novolog®); Venlafaxine (Brand Name: Effexor®); Lorazepam (Brand Name: Ativan®); Ezetimibe (Brand Name: Zetia®); Estrogen (Brand Name: Premarin®); Allopurinol (Brand Name: Zyloprim®); Penicillin (Brand Name: Pen VK®); Sitagliptin (Brand Name: Januvia®); Amitriptyline (Brand Name: Elavil®); Clonidine (Brand Name: Catapres®); Latanoprost (Brand Name: Xalatan®); Lisdexamfetamine (Brand Name: Vyvanse®); Niacin (Brand Name: Niaspan®); Naproxen (Brand Name: Aleve®); Dexlansoprazole (Brand Name: Dexilant®); Gly-buride (Brand Name: Diabeta®); Olanzapine (Brand Name: Zyprexa®); Tolterodine (Brand Name: Detrol®); Ranitidine (Brand Name: Zantac®); Famotidine (Brand Name: Pep-cid®); Diltiazem (Brand Name: Cardizem®); Insulin Glargine (Brand Name: Lantus®); Thyroid (Brand Name: Armour Thyroid®); Bupropion (Brand Name: Well-butrin®); Cetirizine (Zyrtec®); Topiramate (Brand Name: Topamax®); Valacyclovir (Brand Name: Valtrex®); Eszopi-clone (Brand Name: Lunesta®); Acyclovir (Brand Name: Zovirax®); Cefdinir (Brand Name: Omnicef®); Clindamy-cin (Brand Name: Cleocin®); Colchicine (Brand Name: Colcrys®); Gemfibrozil (Brand Name: Lopid®); Guaifen-esin (Brand Name: Robitussin®); Glipizide (Brand Name: Glucotrol®); Irbesartan (Brand Name: Avapro®); Metoclo-pramide (Brand Name: Reglan®); Losartan (Brand Name: Cozaar®); Meclizine (Brand Name: Dramamine®); Met-ronidazole (Brand Name: Flagyl®); Vitamin D (Brand Name: Caltrate®); Testosterone (Brand Name: AndroGel®); Ropinirole (Brand Name: Requip®); Olopatadine (Brand Name: Patanol®); Moxifloxacin (Brand Name: Avelox®); Enoxaparin (Brand Name: Lovenox®); Fentanyl (Brand Name: Duragesic®); Dicyclomine (Brand Name: Bentyl®);

Bisoprolol (Brand Name: Zebeta®); Atomoxetine (Brand Name: Strattera®); Ramipril (Brand Name: Altace®); Temazepam (Brand Name: Restoril®), Phentermine (Brand Name: Adipex® P); Quinapril (Brand Name: Accupril®); Sildenafil (Brand Name: Viagra®); Ondansetron (Brand Name: Zofran®); Oseltamivir (Brand Name: Tamiflu®); Methotrexate (Brand Name: Rheumatrex®); Dabigatran (Brand Name: Pradaxa®); Budesonide (Brand Name: Uceris®); Doxazosin (Brand Name: Cardura®); Desvenla-faxine (Brand Name: Pristiq®); Insulin Lispro (Brand Name: Humalog®); Clarithromycin (Brand Name: Biaxin®); Buspirone (Brand Name: Buspar®); Finasteride (Brand Name: Proscar®); Ketoconazole (Brand Name: Nizoral®); Solifenacin (Brand Name: VESIcare®); Metha-done (Brand Name: Dolophine®); Minocycline (Brand Name: Minocin®); Phenazopyridine (Brand Name: Pyridium®); Spironolactone (Brand Name: Aldactone®); Vardenafil (Brand Name: Levitra®); Clobetasol (Brand Name: Clovate®); Benzonatate (Brand Name: Tessalon®); Divalproex (Brand Name: Depakote®); Dutasteride (Brand Name: Avodart®); Febuxostat (Brand Name: Uloric®); Lamotrigine (Brand Name: Lamictal®); Nortriptyline (Brand Name: Pamelor®); Roflumilast (Brand Name: Dali-resp®); Rabeprazole (Brand Name: Aciphex®); Etanercept (Brand Name: Enbrel®); Nebivolol (Brand Name: Bystolic®); Nabumetone (Brand Name: Relafen®); Nife-dipine (Brand Name: Procardia®); Nitrofurantoin (Brand Name: Macrobid®); Nitroglycerine (Brand Name: NitroStat® SL); Oxybutynin (Brand Name: Ditropan®); Tadalifil (Brand Name: Cialis®); Triamcinolone (Brand Name: Kenalog®); Rivastigmine (Brand Name: Exelon®); Lansoprazole (Brand Name: Prevacid®); Cefuroxime (Brand Name: Ceftin®); Methocarbamol (Brand Name: Robaxin®); Travoprost (Brand Name: Travatan®); Lurasi-done (Brand Name: Latuda®); Terazosin (Brand Name: Hytrin®); Sumatriptan (Brand Name: Imitrex®); Ralox-ifene (Brand Name: Evista®); Mirtazepine (Brand Name: Remeron®); Adalimumab (Brand Name: Humira®); Ben-ztropine (Brand Name: Cogentin®); Baclofen (Brand Name: Gablofen®); Hydralazine (Brand Name: Apreso-line®); Mupirocin (Brand Name: Bactroban®); Propranolol (Brand Name: Inderal®); Varenicline (Brand Name: Chan-tix®); Verapamil (Brand Name: Verelan®); Clotrimazole (Brand Name: Lotrimin®); Phenytoin (Brand Name: Dilan-tin®); Pramipexole (Brand Name: Mirapex®); Liraglutide (Brand Name: Victoza®); Ticagrelor (Brand Name: Bril-inta®); Diclofenac (Brand Name: Voltaren®); Saxagliptin (Brand Name: Onglyza®); Lomitapide (Brand Name: Jux-tapid®); Tizanidine (Brand Name: Zanaflex®); Amphet-amine/Dextro-amphetamine (Brand Name: Adderall®); Zoster Vaccine (Brand Name: Zostavax®); Ezetimibe/Simv-astatin (Brand Name: Vytorin®); Vilazodone (Brand Name: Vybriid®); Hydroxyzine (Brand Name: Vistaril®); Donepe-zil (Brand Name: Aricept®); Acetaminophen (Brand Name: Tylenol®); and Oxcarbazepine (Brand Name: Trileptal®).

In some aspects, the methods and systems described herein may be suitable to analyze samples containing ingre-dients with a molecular weight. In some cases, the molecular weight of the ingredient is 100 Daltons (Da) or less. In some cases, the molecular weight of the ingredient is equal to or less than about 150 kDa, 100 kDa, 75 kDa, 50 kDa, 25 kDa, 10 kDa, 5000 Da, 4000 Da, 3000 Da, 2000 Da, 2500 Da, 1500 Da, 1000 Da, 950 Da, 900 Da, 850 Da, 800 Da, 750 Da, 700 Da, 650 Da, 600 Da, 550 Da, 500 Da, 450 Da, 400 Da, 350 Da, 300 Da, 250 Da, 200 Da, 150 Da, 100 Da, 95 Da, 90 Da, 85 Da, 80 Da, 75 Da, 70 Da, 65 Da, 60 Da, 55 Da, 50 Da, 45 Da, 40 Da, 35 Da, 30 Da, 25 Da, 20 Da, 15 Da, 10 Da, 5 Da. In some cases, the active ingredient is a protein or peptide. In some cases, the active ingredient is a small molecule or a small molecular compound.

In some cases, the pharmaceutical sample may contain one or more excipients. An excipient may be an inactive ingredient that is biologically inert. In some cases, the methods, devices, and systems described herein are capable of distinguishing between the ingredient (e.g. an API) and the one or more excipients. In some cases, the one or more excipients are filtered or otherwise removed from the sample prior to analysis. In some cases, the methods provide for filtering at least a portion of the one or more excipients from the sample prior to analysis. Excipients may include, for example, emulsifiers, stabilizers, suspending agents, binders, viscosity-increasing agents, disintegrants, antiseptics, antimicrobial agents, preservatives, disinfectants, solvents, antioxidants, diluents, sugar coatings, sweeteners, adsorbents, anticaking agents, glidants, emulsion stabilizers, thermal stabilizers, water-absorbing agents, lubricants, chelators, film-formers, granulating agents, extended release agents, stiffening agents, cationic surfactants, non-ionic surfactants, anionic surfactants, detergents, wetting agents, reducing agents, buffering agents, nutrients, dietary supplements, clouding agents, anti-foaming agents, emollients, colorants, coating agents, flavoring fixatives, fillers, gelling agents, humectants, plasticizers, tonicity agents, stabilizing agents, thickening agents, rate-controlling polymers, lyophilization aids, bulking agents, dissolution aids, ointment bases, suppository bases, water-miscible cosolvents, mucoadhesives, dispersing agents, coemulsifying agents, alkalizing agents, acidifying agents, skin penetrants, carbonating agents, sequestering agents, opacifiers, and pigments. Non-limiting examples of excipients may include acacia, alginate, alginic acid, aluminum acetate, benzyl alcohol, butyl paraben, butylated hydroxy toluene, citric acid, calcium carbonate, candelilla wax, croscarmellose sodium, confectioner sugar, colloidal silicone dioxide, cellulose, plain or anhydrous calcium phosphate, carnuba wax, corn starch, carboxymethylcellulose calcium, calcium stearate, calcium disodium EDTA, copolyvidone, castor oil hydrogenated, calcium hydrogen phosphate dehydrate, cetylpyridine chloride, cysteine HCL, crosspovidone, dibasic calcium phosphate, disodium hydrogen phosphate, dimethicone, erythrosine sodium, ethyl cellulose, gelatin, glyceryl monooleate, glycerin, glycine, glyceryl monostearate, glyceryl behenate, hydroxy propyl cellulose, hydroxyl propyl methyl cellulose, hypromellose, HPMC phthalate, iron oxides or ferric oxide, iron oxide yellow, iron oxide red or ferric oxide, lactose hydrous or anhydrous or monohydrate or spray dried, magnesium stearate, microcrystalline cellulose, mannitol, methyl cellulose, magnesium carbonate, mineral oil, methacrylic acid copolymer, magnesium oxide, methyl paraben, povidone or polyvinylpyrrolidone (PVP), polyethylene glycol (PEG), polysorbate 80, propylene glycol, polyethylene oxide, propylene paraben, polaxamer 407 or 188 or plain, potassium bicarbonate, potassium sorbate, potato starch, phosphoric acid, polyoxy 140 stearate, sodium starch glycolate, starch pregelatinized, sodium crossmellose, sodium lauryl sulfate, starch, silicon dioxide, sodium benzoate, stearic acid, sucrose, sorbic acid, sodium carbonate, saccharin sodium, sodium alginate, silica gel, sorbiton monooleate, sodium stearyl fumarate, sodium chloride, sodium metabisulfite, sodium citrate dehydrate, sodium starch, sodium carboxy methyl cellulose, succinic acid, sodium propionate, titanium dioxide, talc, triacetin, and triethyl citrate.

The pharmaceutical sample may additionally contain one or more impurities. An impurity may be, for example, formed during the manufacturing process such as unreacted starting material or intermediates or byproducts. Impurities may include degradation products such as those formed during the synthetic process, during storage, during formulation of the dosage form or during aging of the drug. Additional impurities may include inorganic impurities, stereoisomeric impurities, structural isomer impurities, reagents, ligands, catalysts, heavy metals, filter aids, charcoal, and residual solvents. In some cases, the impurities are formulation-related impurities such as method related, environmental related (e.g., exposure to adverse temperatures, light (e.g., U. V.), or humidity), and dosage form related such as mutual interaction amongst ingredients, and functional group related degradation (e.g., ester hydrolysis, hydrolysis, oxidative degradation, photolytic cleavage, or decarboxylation). In some cases, the methods, devices, and systems described herein are capable of distinguishing between an API and one or more impurities contained in the sample.

In some instances, the sample is a cosmetic. Cosmetics may include, for example, a cream or a gel. In other instances, the sample is a food, beverage, or a nutritional supplement. In some instances, the sample comprises chemical precursors used in the synthesis of other substances or materials. In some instances, the sample is a sample suspected of containing illicit drugs. In some instances, the sample comprises stimulating drugs, depressant drugs, opioids, or hallucinogenic drugs. As non-limiting samples, the sample may comprise cathinone, GHB, heroin, 1-butyl-3-(1-naphothoyl)indole (JWH-073), psilocybin, or LSD. In some instances, the sample comprises depressants or sedatives. In some instances, the sample is a substance being investigated as a possible pharmaceutical. For example, the sample may be a research sample that is still in a research and development stage. In some instances, the sample may be a sample (e.g. drug sample) in a pre-clinical or clinical-trial stage.

Embodiments

In some aspects, a sample, a subset of a sample, or a portion of the sample to be analyzed may be provided by any method (e.g., by mailing a single prescription pill to a service provider). In some instances, the sample may be received from an entity or an individual disclosed herein, or a provider of the sample at predetermined intervals. For example, the sample may be received every day, every 3 days, every week, bi-weekly, every month, every 3 months, every 6 months, every year, or less frequently. In some instances, a single sample (e.g. a single pill) may be received at a time (e.g. at the predetermined intervals). Alternatively, two, three, four, five, six, seven, eight, nine, ten, twenty, or more samples may be received at a time (e.g. at the predetermined intervals). The samples may comprise a same ingredient (e.g. same API). Alternatively, differing samples with differing ingredients (e.g. differing APIs) may be received at a time.

A provider of the sample may be desirous of verifying or confirming the identity of the sample. In some instances, a medical provider, pharmacy, pharmacist, an end user, medical profession or employee in the medical industry or a member of the supply chain from development of a pharmaceutical to the dispensing of the pharmaceutical to an end user can be referred to herein as an entity. For example, an end-user may be prescribed a pharmaceutical sample (e.g., a medication) and the entity providing the prescribed pharmaceutical may want to confirm the composition of the sample. In another aspect, an intermediary may want to confirm the composition of a sample before providing units of a medication batch to an end user. For example, an entity may wish to identify an inactive ingredient, or multiple inactive ingredients in a sample. In other examples, the entity may wish to confirm that a specific amount of an active ingredient is present in the sample. In yet other examples, the entity may wish to confirm the purity of the sample (i.e., the absence of impurities in the sample). The sample may be tested utilizing the methods, devices, and systems as set forth herein to determine one or more characteristics of the sample. The one or more characteristics may include the identity of a molecule in the sample, the quantity of a molecule in the sample, or both. In some cases, the one or more characteristics may include a chemical identity (ID) of the sample, or a chemical of the sample. A chemical ID may refer to a precise chemical identity of the sample, or a chemical of the sample. In some instances, a chemical ID may refer to a unique signature of the chemical. Optionally, the chemical ID may refer to a particular molecular configuration. In some instances, the chemical ID may refer to a unique spectrum of the sample (or a chemical of the sample). In some instances, no two chemicals may have a same signature (e.g. chemical ID). In some instances, a chemical ID may refer to a name in chemical nomenclature or a registry number assigned by an organization service, such as the chemical abstract service (CAS). In some instances, the chemical ID may provide insight into impurities existing in the sample.

In some aspects, a sample or a subset of a sample or batch is obtained. The sample may be received and analyzed for quality assurance for the end-user or distributing business of a product. The sample or a portion of the sample to be analyzed may be provided by any method. In some instances, a sample, a subset of a batch, a unit of a medication, a unit of a sample, and a subset of a sample can be used interchangeably.

The methods described herein may be particularly suited to analyzing samples of varying shapes and/or sizes. Optionally, the methods described herein may be particularly suited to analyzing samples of varying densities. In some instances, the methods described herein may be particularly suited to analyzing samples received from differing manufacturers of the sample. For example, the methods may be suitable for analyzing the composition of different samples containing a same ingredient but of differing size and shape without a calibration step prior to the analysis. For example, the methods may be suitable for analyzing the composition of different samples containing a same ingredient but of differing size and shape without a calibration step between analyzing a first sample and analyzing a second sample. For example, the methods may be capable of identifying the API for a plurality of different samples without separate calibration. For example, the methods may be capable of identifying a quantity of an API for a plurality of different samples without separate calibration. In this instance, the plurality of different samples may comprise different pills. In some cases, the plurality of different samples may comprise different shapes and different sizes. In some cases, the plurality of different samples may be dissolved or suspended in a solvent prior to the analysis. The sample(s) substantially as described throughout, may comprise an ingredient of interest and may be in any given form, e.g. solid, liquid, gelatinous, etc.

In some aspects, the methods involve preparing a liquid sample for analysis. In particular cases, the methods involve dissolving a sample to generate a solution. In one example, the sample may be provided in a solid form (e.g., a pill or tablet). The solid sample can be dissolved in a liquid to generate a solution for analysis. Dissolving the sample may involve crushing or pulverizing the sample prior to the addition of one or more solvents. For example, a pill or tablet may be crushed with a steel ball in a tube prior to addition of a solvent. In other examples, the sample may be crushed in the presence of a solvent. In some instances, the liquid sample comprises an extract of the sample. In other cases, the liquid sample may be a liquid solution. In other cases, the liquid sample may be a liquid suspension. In some instances, the liquid sample may be further processed prior to analysis. For example, the liquid sample may be placed in a filter such as a spin filter to get a final extract utilized in the analysis.

In particular aspects, the methods provide for the use of a solvent. The solvent may be used to dissolve a sample to generate a solution for analysis. In some instances, enough solvent may be added to ensure an ingredient (e.g. API) of the sample is dissolved. In some instances, enough solvent may be added to ensure all of the ingredients (e.g. API) of the sample are dissolved. In some instances, the ingredient may be distributed in the solution. In some instances, the ingredient may be distributed homogeneously within the solution. Accordingly, a subsample (e.g. component, part, etc) of the solution may be representative of the whole. The use of solvents and/or the crushing may make a particular size and/or shape of the sample irrelevant for purposes of analysis.

Optionally, the one or more characteristics of the sample from a given batch or subset of a batch may be presented on a report and provided to the end-user or distributing business of units from that batch. In some cases, the report may present the composition of the sample. For example, the report may present the identity of one or more molecules present in the sample, the quantity of one or more molecules present in the sample, or both. In some cases, the report may indicate the presence of an active ingredient present in the sample and additionally, the presence of one or more excipients, one or more impurities, and the like. In some cases, the report may provide a list of all of the ingredients found within a sample and/or their quantities. In some cases, the report may confirm that the sample is of the intended composition (e.g., is authentic). In other cases, the report may confirm that the sample is of an unintended composition (e.g., counterfeit). The report may be presented in any number of different ways, including alphanumerical presentation, graphical presentation and the like. In some cases, the report may include spectral data represented graphically. In some cases, the report may summarize the results of the analysis in any number of lists, tables, charts, and the like. The report may be presented to an end-user or distributing business in a tangible form (e.g., on a sheet of paper) or may be presented to in an electronic format. Electronic reports may be accessed via, e.g., the Internet or by e-mail. In some cases, the report is presented for display on a screen. In some cases, the report is uploaded to a database. Optionally, information contained in the database may be viewed or downloaded by a user. The database may comprise a compilation of reports containing information regarding the composition of a plurality of different samples obtained from various sources. The database in some instances may provide utility in identifying sources of counterfeit or improperly formulated pharmaceutical products. In other embodiments, where a unit of a medication is validated, a unit from a batch or subset of a batch from which the unit of medication that was tested is from is dispensed to an end user. In some cases, a validated unit of a medication or validated medication is provided to an end user.

Disclosed herein are systems for performing the methods described herein. The systems may include any number of devices that operate individually or in concert to perform the described methods. The minimum components of the system are described herein, however, it shall be understood that additional components may be used. Although examples are herein described, it is to be further understood that any order or arrangement of the system components may be utilized.

In an aspect, the present disclosure provides a system for dispensing or distributing a validated medication to an end-user or distributing business, comprising: a computer, in communication with the communication interface, wherein the computer comprises one or more computer processors and a computer readable medium comprising machine-executable code that, upon execution by the one or more computer processors, implements a method comprising: (a) receiving, over the communication network, a prescription for a medication from a physician, or an order for a non-prescription medication or medication-like product, wherein the medication is obtained and analyzed for an ingredient in the medication using an analytical test, wherein the medication is from a medication batch or subset of a batch; and (b) comparing the ingredient to a reference or derivative thereof; and (c) providing the validated medication to the end-user or distributing business, wherein the validated medication is from the medication batch or subset of a batch.

In another aspect, the present disclosure provides a system for validating a medication, comprising: (a) an instrument for analyzing an ingredient of a medication in an analytical test, wherein the medication is from a medication batch; and (b) a computer, in communication with the communication interface, wherein the computer comprises one or more computer processors and a computer readable medium comprising machine-executable code that, upon execution by the one or more computer processors, implements a method comprising: (i) receiving, over the communication network, a prescription for the medication from a physician or an order for a medication product not requiring a prescription, for analyzing the ingredient using the instrument in (a); (ii) comparing the ingredient to a reference or derivative thereof; and (ii) providing a validated medication to an end-user.

In another aspect, the present disclosure provides a system for providing a validated unit of a medication to an end-user or distributing business, comprising: one or more processors and a non-transitory computer readable medium comprising instructions operable, when executed by the one or more processors, to cause the system to: receive, over a communication network, a prescription for the medication; dissolving at least a portion of the unit of the medication from a batch or subset of a batch of the medication, thereby generating a solution; analyze an ingredient of the unit of the medication using an analytical test thereby generating an analysis result, wherein the solution comprises the ingredient; comparing the analysis result to a reference or derivative thereof thereby generating a comparison result; determining a validation status of the medication batch or subset of a batch based on the comparison result; and providing the validated unit of the medication to the end-user or distributing business, wherein the validated unit of the medication is from the medication batch or subset of a batch. The validated unit may be a single pill, a single tablet, a single capsule, a single sample, or any multiple or combination thereof.

In some aspects, the methods and systems provide improvements to existing methods and systems. These improvements may include, without limitation, enhanced robustness to supply-chain vulnerabilities, tighter limits on variation across ostensibly equivalent medications, tighter limits on variation across ostensibly identical medications, universal application to pharmaceutical end-products, faster sample-to-analysis time, improved accuracy, improved precision, and decreased costs.

Rapid Analysis

In some cases, the methods and systems provide for rapid sample processing time. For example, the sample processing time to generate a sample solution may be on the order of less than about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, or about 15 minutes. In some cases, the sample analysis time (e.g., Raman collection time) can be on the order of less than about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, or about 15 minutes. In some cases, the sample-to-analysis time (e.g., from the beginning of sample processing time to the end of the Raman collection time) can be on the order of less than about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, or about 30 minutes.

Accuracy

In some cases, the methods and systems provide for improved accuracy. Accuracy is a measurement of how closely a value conforms to the correct value. In some cases, the methods, devices, and systems analyze the quantity or purity of an ingredient in the sample with an accuracy of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0% or greater than 10.0%.

In some cases, the methods and systems determine the amount of an ingredient (e.g., an API) in the sample with an error rate equal to or less than about 10%, 9.9%, 9.8%, 9.7%, 9.6%, 9.5%, 9.4% 9.3%, 9.2%, 9.1%, 9.0%, 8.9%, 8.8%, 8.7%, 8.6%, 8.5%, 8.4%, 8.3%, 8.2%, 8.1%, 8.0%, 7.9%, 7.8%, 7.7%, 7.6%, 7.5%, 7.4%, 7.3%, 7.2%, 7.1%, 7.0%, 6.9%, 6.8%, 6.7%, 6.6%, 6.5%, 6.4%, 6.3%, 6.2%, 6.1%, 6.0%, 5.9%, 5.8%, 5.7%, 5.6%, 5.5%, 5.4%, 5.3%, 5.2%, 5.1%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1% or less.

In some cases, the methods and systems provide for improved precision. Precision may refer to the closeness of two or more measurements and may reflect the amount of variability in the system. In some cases, the methods, devices, and systems analyze the quantity of an ingredient in the sample with a precision equal to or less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0% or greater than 10.0%.

In some aspects, the methods and systems may improve the ability to detect an impurity in a sample. In some aspects, the methods, devices, and systems may improve the ability to distinguish between an impurity and an active ingredient in a sample. In some cases, the methods and devices may be capable of detecting an impurity in a sample containing the impurity and an active ingredient. In some cases, the methods and devices are capable of detecting an impurity in a sample that contains about 0.05%, 0.1%, 0.15%, 0.2%, 0.25%, 0.3%, 0.35%, 0.4%, 0.45%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% of the impurity.

Solvents

In some aspects, the methods involve preparing a liquid sample for analysis. In particular cases, the methods involve dissolving a sample to generate a solution. In one example, the sample may be provided in a solid form (e.g., a pill or tablet). The solid sample can be dissolved in a liquid to generate a solution for analysis. Dissolving the sample may involve crushing or pulverizing the sample prior to the addition of one or more solvents. For example, a pill or tablet may be crushed with a steel ball in a tube prior to addition of a solvent. In other examples, the sample may be crushed in the presence of a solvent. In some instances, the liquid sample comprises an extract of the sample. In other cases, the liquid sample may be a liquid solution. In other cases, the liquid sample may be a liquid suspension. In some instances, the liquid sample may be further processed prior to analysis. For example, the liquid sample may be placed in a filter such as a spin filter to get a final extract utilized in the analysis.

In particular aspects, the methods provide for the use of a solvent. The solvent may be used to dissolve a sample to generate a solution for analysis. In some instances, enough solvent may be added to ensure an ingredient (e.g. API) of the sample is dissolved. In some instances, enough solvent may be added to ensure all of the ingredient (e.g. API) of the sample is dissolved. In some instances, the ingredient may be distributed in the solution. In some instances, the ingredient may be distributed homogeneously within the solution. Accordingly, a subsample (e.g. component, part, etc) of the solution may be representative of the whole. The use of solvents and/or the crushing may make a particular size and/or shape of the sample irrelevant for purposes of analysis.

In some cases, the choice of solvent may provide improvements to traditional analytical methods. Non-limiting examples of solvents that may be amenable to performing the methods described herein include: pentane; cyclopentane; hexane; cyclohexane; benzene; toluene; 1,4-dioxane; chloroform; diethyl ether; dichloromethane (DCM), tetrahydrofuran (THF); ethyl acetate; acetone; dimethylformamide (DMF); acetonitrile (MeCN); dimethyl sulfoxide (DMSO); DMSO/DMF; nitromethane; propylene carbonate; formic acid; n-butanol; isopropanol (IPA); n-propanol; ethanol; methanol; acetic acid; water; acetaldehyde; 1,2-butanediol; 1,3-butanediol; 1,4-butanediol; 2-butoxyethanol; butyric acid; diethanolamine; diethylenetriamine; dimethoxyethane; ethylamine; ethylene glycol; furfuryl alcohol; glycerol; methyl diethanolamine; methyl isocyanide; 1-propanol; 1,3-propanediol; 1,5-pentanediol; 2-propanol; propanoic acid; propylene glycol; pyridine; triethylene glycol; 1,2-dimethylhydrazine; unsymmetrical dimethylhydrazine; hydrazine; hydrofluoric acid; hydrogen peroxide; nitric acid; sulfuric acid; 1-butanol; 2-butanol; 2-butanone; t-butyl alcohol; carbon tetrachloride; chlorobenzene; 1,2-dichloroethane; diethylene glycol; bis(2-methoxyethyl)ether (diglyme); 1,2-dimethoxy-ethane (glyme, DME); heptane; hexamethylphosphoramide (HMPA); hexamethylphosphorous triamide (HMPT); methyl t-butyl ether (MTBE); methylene chloride; N-methyl-2-pyrrolidinone (NMP); nitromethane; petroleum ether (ligroine); triethyl amine; o-xylene; m-xylene; p-xylene; 1-chlorobutane; N,N-diisopropylethylamine; Cap B (80% tetrahydrofuran, 10% pyridine, 10% 1-methylimidazole); Cap Mix A (90% tetrahydrofuran, 10% acetic anhydride); Cap Mix A (80% tetrahydrofuran, 10% acetic anhydride, 10% 2,6-lutidine); Cap Mix A (80% tetrahydrofuran, 10% acetic anhydride, 10% pyridine); trifluoroacetic acid; 1,1,1-trichloroethane; 1,2-dichloroethane; 1-octanol; 2,2,4-trimethylpentane; 2-butanone; 2-methoxy ethanol; 2-methyl-1-propanol; 3-methyl-1-butanol; 4-methyl-2-pentanone; benzyl alcohol; butyl acetate; carbon disulfide; carbon tetrachloride; chlorobenzene; dichloromethane; diisopropyl ether; formamide; nitrobenzene; nitromethane; tert-butanol; tetrachloroethylene; trichloroethylene; 1,1,2,2-Tetrachloroethane; 1,2,3,4-Tetrahydronaphthalene reagent grade, 1-hexanol; 2-butoxyethyl acetate; 2-methoxyethyl acetate; 2-pentanone; 3-pentanone; cyclopentane; decahydronaphthalene; diethylene glycol diethyl ether; ethylene glycol diethyl ether; isopentyl acetate; methyl acetate; methyl formate; nitromethane; propionaldehyde; tert-butyl acetoacetate; trichloroethylene; triethyl orthoformate; 1,2,4-trichlorobenzene; 1,2-dichlorobenzene; 1,2-dichloroethane; 1,2-dimethoxyethane; 1,3-dioxolane; 1,4-dioxane; 1-chlorobutane; 1-methoxy-2-propanol; 2-(2-butoxyethoxy) ethyl acetate; 2,2,4-trimethylpentane; 2-butanone; 2-butoxyethanol; 2-ethoxyethanol; 2-ethylhexyl acetate; 2-heptanone; 2-methoxy ethanol; 2-methyl-1-propanol; 2-methylbutane; 2-methyltetrahydrofuran; 3-methyl-1-butanol; 4-]methyl-2-pentanone; 5-methyl-2-hexanone; anisole; benzonitrile; decane; dibutyl ether; formaldehyde diethyl acetal; diethylene glycol butyl ether; diethylene glycol monoethyl ether; diethylene glycol monoethyl ether acetate; dodecane; ethyl 3-ethoxypropionate; ethylbenzene; 2-propoxyethanol; hexadecane; isopropyl acetate; methyl cyclohexane; N,N-dimethylacetamide; nonane; propyl acetate; TEBOL 99; or tetrahydropyran.

In some instances, water may be added to the solvent to prevent absorption from the air and improve the precision of the analysis. Alternatively or in addition, water may be added to lower a vapor pressure of the solvents. For example, water may be added to the solvent at about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.2%, 1.4%, 1.6%, 1.8%, 2%, 2.5%, 3%, 3.5%, 4%, 4.5%, 5%, 7%, 10%, or more than 10%.

In some cases, the solvent is non-volatile. Volatility may refer to a tendency of a substance to vaporize and may be directly related to the vapor pressure of the solvent. At a given temperature, a solvent with a higher vapor pressure vaporizes more readily than a substance with a lower vapor pressure. In some cases, the solvent has a vapor pressure of less than 40 mm Hg at 20° C. Non-limiting examples of solvents with a vapor pressure of less than 40 mm Hg at 20° C. include acetic acid; acetyl acetone; 2-aminoethanol; aniline; anisole; benzonitrile; benzyl alcohol; 1-butanol; 2-butanol; 1-butanol; 2-butanone; chlorobenzene; cyclohexanol; cyclohexanone; diethylene glycol; dimethylformamide (DMF); dimethylsulfoxide (DMSO); ethyl acetoacetate; ethylene glycol; 1-hexanol; 1-pentanol; 2-pentanol; 3-pentanol; 1-propanol; pyridine; toluene; 1-Methyl-2-pyrrolidinone; propylene carbonate; 2-Pyrrolidinone; Pyrrolidinone; 1,3-Butanediol; water; p-xylene; or any combination of the aforementioned solvents with other solvents or solutions. In some cases, the solvent has a vapor pressure of less than 100, 90, 80, 70, 60, 50, 40, 30, 20, 10, or 5 mm Hg at 20° C.

In some aspects, the solvent is selected to have one or more of the following properties: (1) low volatility; (2) high drug solubility; (3) low excipient solubility; (4) low toxicity; and (5) a favorable spectra which enables precise analysis. In some cases, the solvent is selected such that the one or more ingredients are dissolved in the solvent but the one or more excipients are not dissolved in the solvent. In some cases, the undissolved excipients can be filtered or otherwise removed from the sample.

In some aspects, the solvent is selected based on the one or more ingredients present in the sample. The solvent may be selected to have high drug solubility. In some cases, the solvent has a drug solubility of at least about 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 100 mg/mL, 200 mg/mL, 300 mg/mL, 400 mg/mL, 500 mg/mL, 600 mg/mL, 700 mg/mL, 800 mg/mL, 900 mg/mL, 1000 mg/mL or greater.

Drug Variability

Existing drugs, consumables, or medications may have variability, e.g., in active ingredients such as active pharmaceutical ingredients. In some instances, individuals or entities (e.g., individual end users of the consumables or medications) may have uncertainty or distrust over the quality consistency of medication. In some instances, counterfeit consumables or medications may exist such that the medications are ineffective, less effective than indicated, or even harmful. The present disclosure provides methods for validating medications or drugs prior to sale of the medications. In some instances, the medications may be chemically validated. Alternatively or in addition, the medications may be optically validated. In some instances, the medications may be validated or verified with a laser-based system (e.g., spectroscopy or Raman spectroscopy). In addition, wet-lab and software innovations may be integrated. The medication may be validated or analyzed (e.g., for dosage analysis) with an error less than 0.1%, 0.2%, 0.5%, 1%, 2%, 5%, 10%, 15%, or 20%. The medication may be validated or analyzed (e.g., for dosage analysis) to ensure that variability in dosage or weight is no more than 0.1%, 0.2%, 0.5%, 1%, 2%, 3%, 4%, 5%, 6%, 7%, 8%, 9%, 10%, 15%, or 20%. Variability cutoffs for each drug may also be established based in part on a regulatory cutoff for allowed variability and optionally could be made more stringent. The medication may be validated or analyzed quickly, such as in less than a week, less than 3 days, less than a day, less than 16 hours, less than 8 hours, less than 4 hours, less than 2 hours, less than an hour, less than 30 minutes, less than 15 minutes, less than 5 minutes, less than 2 minutes, less than a minute, or any amount of time there between. The validation or analysis of the medication may comply with ISO 17025 standards. The validation or analysis of the medication may comply with USP <905> standards as to content and uniformity, such that if a tested batch or subset of a batch of medication is measured to fall outside of the bounds indicated by the standards, then it is marked as failing the validation test, rejected for human consumption, and returned to the manufacturer for refund. Alternatively, or in addition, in some aspects, the validation standards can be more stringent than USP <905> and/or other FDA and other regulatory standards. In some aspects, if a tested batch or subset of a batch of medication is measured to fall within the bounds indicated by the standards, then it is marked as validated. In some embodiments, validated medications are provided to an end user or distributing business or categorized and stored. In some aspect, the entity testing a sample is a pharmacy. In some embodiments, a pharmacy chemically validates medication batches or subset of a batches before dispensing to consumers or distributing businesses.

Medications comprising an allegedly same active ingredient may vary, in some cases substantially, from one another. In some instances, medications may comprise an incorrect amount of the ingredient of interest or incorrect types of inactive ingredients such as fillers. The variability may in some instances lead to harm to a user of the medication. For example, taking medication may lead to seizures or adverse effects due to the incorrect amount of the active ingredient and/or inclusion of wrong fillers. For example, case studies of anti-epileptic drugs (AEDs) have shown a link between breakthrough seizures and generic AED substitution, and that AED prescription filling itself was associated with a 2.3-fold elevated odds of seizure-related events.

A substantial percentage of people are aware of, or may believe, that there is variability in the medication they are taking, even for a same prescription. Patients taking prescription medications may notice a difference in how they felt or how effective their medication was after refilling a prescription. In some instances, people may believe that they have received counterfeit medication. In other cases, people may believe that they have received medication that had incorrect dosage.

Supply Chain Vulnerabilities

Supply chain vulnerabilities may also affect variability of medication. A supply chain may comprise manufacturing and distribution of medications. Manufacturing of medications may comprise processing raw materials to produce active ingredients, and processing active ingredients and inactive ingredients to produce a final product. Distribution may comprise transporting a final product to national and regional wholesalers and to smaller wholesalers, transporting the final product between national and regional wholesalers and smaller wholesalers, transporting the final product to hospitals and pharmacies, and distributing the final product to the end user of the medication. In general, medication produced through highly complex supply chains may be expected to have variability. As illustrated, in FIG. 1, issues may be introduced anywhere along the supply chain. For example, raw materials may include ingredients of poor quality. As another example, the final product may be formulated improperly. As another example, shipping and/or storage of the raw materials to final product, or of the final product to intermediaries, or of the final product from intermediaries to end users, may occur under improper conditions. As another example, packaging and labeling may be subject to improper diversion or substitution.

By performing validation of the medication prior to selling to a user, problems may be detected and identified wherever they originate along the supply chain. The medication may be validated such that an end user of the medication may only receive validated and/or consistent medication having an active ingredient within an acceptable range or amount, and/or appropriate fillers and other important properties like proper dissolution. Medication that has failed the validation process or that has been identified as falling outside an acceptable range or amount may be rejected for distribution to the end user of the medication.

Validation Certificates of Analysis

FIG. 2 illustrates an exemplary embodiment of dispensing medication, in accordance with embodiments. As shown, a pill, representative of a batch or subset of a batch, may be tested for quality and/or consistency. For example, the pill or medication, may be tested to ensure that an amount of the active ingredient is within a desired range, and/or stated range (e.g., the amount of the label claim). For example, the pill or medication, may be tested to ensure that an amount of the inactive ingredient is within a desired range, and/or stated range. Optionally, a certificate of analysis may be provided for the drug, listing the ranges for each of the active ingredients and/or the inactive ingredients. Each of the active ingredients may be ensured to be within 1%, 2%, 5%, 10%, or 20% of the desired or indicated range. Each of the inactive ingredients may be ensured to be within 1%, 2%, 5%, 10%, or 20% of the desired or indicated range. In some instances, less than 0.01%, 0.01%, 0.1%, 1%, 2%, 5%, 10%, 15%, 20%, 30%, 40%, 50%, or values therebetween of the medications of a batch or subset of a batch may be analyzed to provide the validation or assurance of an amount of active or inactive ingredients or other properties in each of the medications of the batch or subset of a batch. Optionally, the batch or subset of a batch may comprise a number of pills equal to or more than about 100, 500, 1,000, 5,000, 10,000, 20,000, 50,000, 100,000, 200,000, 500,000, 1,000,000, 2,000,000, 5,000,000 or 10,000,000; or less than about 5, 10, 15, 20, 25, 30, 40, 50, 60, 70, 80, 90, 100, 120, 140, 160, 180, 200, 250, 300, 500, 2,000, or 15,000 pills. Just as consumers would prefer to have greater information regarding a consumable or food product, medications having greater information would cater to the information age where users desire more information. Accordingly, the present disclosure provides a method of offering a certificate of analysis for the medication comprising a certificate of analysis for the medication with an exact range of the active ingredient and/or range of inactive ingredients and other properties like dissolution. Such an exemplary certificate of analysis may provide value differentiation in the market for medications.

In some embodiments, a certificate of analysis may provide information, including active ingredient (API), authenticity and exact dosage of the API, major inactive ingredients, drug dissolution information (e.g., results of a disintegration test and the drug release time).

Advantages and Analysis

There are advantages of methods of the present disclosure. Validating and selling validated medication may provide numerous advantages. For example, it may ensure that the medication is safe for an end user to take. As another example, it may ensure that the medication a user is taking is consistent such that there is minimal variation in effect. In some instances, the validated or verified medication may be sold online such that consumers are able to receive validated, consistent, and safe medication in a convenient method, e.g., by ordering from the comfort and convenience of their homes.

Medications were previously not validated for a myriad of reasons. As one example, apathy may play a role. Drug manufacturers and pharmacies may rely on the regulatory agencies to ensure and enforce quality and consistency guidelines. In some instances, not having medication may provide ability for pharmacies and/or drug manufacturers to blame another side, giving them plausible deniability should something go wrong. In some instances, validating a small batch or subset of a batch of medication may be expensive or complicated. For example, for a given drug, there may be hundreds of different formulations comprising different ingredients (e.g. inactive ingredients).

Further, with regard to testing medication, HPLC lab analysis of medications may incur significant monetary and time costs. For example, a typical HPLC lab analysis of medication (e.g., ibuprofen, acetaminophen, and citalopram) may cost $500 to $1000 per pill, with a $2000 to $4000 setup fee. The HPLC lab analysis may require a user provided standard. The HPLC lab analysis may require a turnaround (sample-to-answer) time of several days or weeks. Additionally, there are impurities which are undetectable by HPLC. In generally, many common impurities that may be present in medications may be undetectable by HPLC analysis approaches. For example, HPLC analysis cannot distinguish between a bupropion standard drug and bupropion impurity A, because the two are isomers of each other. In contrast, other methods such as Raman spectroscopy may be able to easily detect the bupropion impurity and distinguish it from the bupropion standard drug.

Using methods and systems of the present disclosure, any pill, capsule, or product (e.g. drug or medication) may be analyzed for quality and/or consistency. The precision (e.g., of the measured ingredients, such as active or inactive ingredients) of analysis may be within 0.01%, 0.02%, 0.05%, 0.1%, 0.2%, 0.5%, 1%, 2%, 5%, or 10%. The analysis may be completed within a period of time (e.g., time-to-answer) of less than a week, less than 3 days, less than a day, less than 16 hours, less than 8 hours, less than 4 hours, less than 2 hours, less than an hour, less than 30 minutes, less than 15 minutes, less than 5 minutes, less than 2 minutes, less than a minute, or any amount of time therebetween. The system may be advantageously scalable in that it may be simple to operate such that an operator having advanced training or advanced degrees are not necessary. For a given drug, a system may undergo calibration that can be completed in a period of time less than a week, less than 3 days, less than a day, less than 16 hours, less than 8 hours, less than 4 hours, less than 2 hours, less than an hour, less than 30 minutes, less than 15 minutes, less than 5 minutes, or any amount of time therebetween. The system may be capable of detecting any and all impurities, including isomer impurities. The system may be capable of performing validation that complies with ISO 17025 standards.

The methods and systems provided herein may be used to validate prescription drugs, over-the-counter (OTC) drugs, and/or supplements. For example, prescription drugs may be validated for a number of types of medications, including blood pressure, cholesterol, anti-depressants, diabetes, erectile dysfunction (ED), and cancer. End users of such prescription drugs may have concerns about having high quality medications.

The present systems and methods may provide a validated or verified product that users can trust at a cheaper price than name brand medications. Validated prescription drugs (brand name or generic) may be sold at a higher margin compared to their counterparts sold through retail pharmacies or legal online pharmacies. Validated prescription drugs (brand name or generic) may be sold in a premium marketplace with high demand for them. The certification of such validated prescription drugs (brand name or generic) may add value and margin to their marketability. Validated prescription drugs (brand name or generic) may be sold as part of a discount premium market. Validated prescription drugs may be sold as part of a branded generics market, at a price point less than that of name brand drugs but greater than that of generic drugs. In some cases, economies of scale, intrafirm cross-subsidization, and/or other economic mechanisms may be such that validated medications can be sold at a price-point below that of corresponding non-validated medications.

Figure 3:
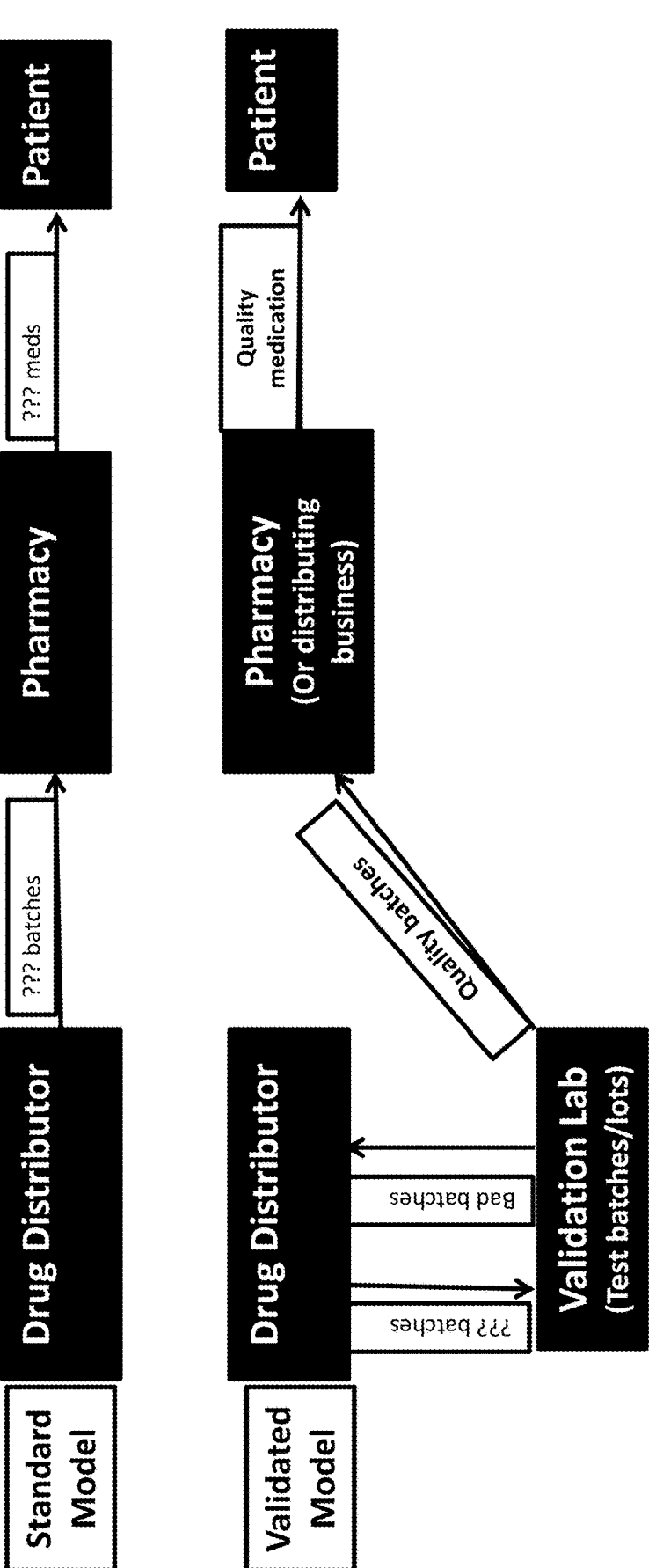
FIG. 3 illustrates an analytical workflow of the medication validation, in accordance with embodiments.

FIG. 3 illustrates an analytical workflow of the medication validation, in accordance with embodiments. A pill may be pre-processed for analysis by chemistry methods including proprietary solvents. Next, spectrometry and/or custom hardware may be used to generate a spectrometric profile of the active ingredients and inactive ingredients present in the medication. Next, software incorporating algorithms may analyze the spectrometric profiles to identify, quantify, and verify the quality and/or consistency of the medication. Such an analytical workflow may be capable of analyzing the medication with a rapid sample-to-answer time of, for example, about 15 minutes.

Validation Outcome

When a medication is tested, one of several different outcomes may be possible. For example, a batch may fail to comply with statutory or regulatory standards, a batch may barely meet statutory or regulatory standards, a batch may surpass statutory or regulatory standards, or a batch may surpass statutory or regulatory standards by a significant margin (e.g., by having low variability and high accuracy).

In some instances, the batches which have undergone analysis using the methods and systems provided herein may be distributed according to a criteria. While four different outcomes were provided for illustrative purposes, it is to be understood that fewer or more possible outcomes may be possible. For example, the size of a set of possible outcomes may be equal to 2, e.g., for passing statutory or regulatory standards or not passing statutory or regulatory standards. As another example, the size of a set of possible outcomes may be equal to 3, e.g., for meeting statutory or regulatory standards, surpassing statutory or regulatory standards, and failing statutory or regulatory standards. As another example, the size of a set of possible outcomes may be equal to 4, e.g., for barely meeting statutory or regulatory standards, being moderately good relative to statutory or regulatory standards, being excellent relative to (significantly surpassing) statutory or regulatory standards, and failing statutory or regulatory standards. After having undergone the testing and analysis process, the drugs may be identified according to the determined criteria. The identification may indicate how the batch performed under the analysis. Subsequently, the identified medications may be provided to users, consumers or distributing businesses.

In some aspects, at least 0.05%, 0.1%, 0.15%, 0.2%, 0.25%, 0.3%, 0.35%, 0.4%, 0.45%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% of the composition of a sample corresponds to a reference composition or derivative thereof. In some aspects, at least 0.05%, 0.1%, 0.15%, 0.2%, 0.25%, 0.3%, 0.35%, 0.4%, 0.45%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% of an ingredient of a sample corresponds to a reference ingredient or a derivative thereof. In some aspects, a concentration of an ingredient in a sample is within at least 0.05%, 0.1%, 0.15%, 0.2%, 0.25%, 0.3%, 0.35%, 0.4%, 0.45%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% of a reference concentration or derivative thereof. In some aspects, a quantity of an ingredient in a sample is within at least 0.05%, 0.1%, 0.15%, 0.2%, 0.25%, 0.3%, 0.35%, 0.4%, 0.45%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% of a reference quantity or derivative thereof. In some aspects, a mass of a sample is within at least 0.05%, 0.1%, 0.15%, 0.2%, 0.25%, 0.3%, 0.35%, 0.4%, 0.45%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% of a reference mass or derivative thereof.

In some aspects, a concentration of an ingredient in a sample, a quantity of an ingredient in a sample, a mass of a sample, or a composition of a sample is within at least 0.05%, 0.1%, 0.15%, 0.2%, 0.25%, 0.3%, 0.35%, 0.4%, 0.45%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% of an ingredient in a reference, a quantity of an ingredient in a reference, a mass of a reference, or a composition of a reference.

In some aspects, a sample's validation status is validated if a concentration of an ingredient in a sample, a quantity of an ingredient in a sample, a mass of a sample, or a composition of a sample is within at least 65%, 70%, 75%, 80%, 85%, 90%, 95%, 99% or greater than 99% of an ingredient in a reference, a quantity of an ingredient in a reference, a mass of a reference, or a composition of a reference.

In some aspects, a validated medication is dispensed to an end user or entity if a concentration of an ingredient in a unit of a medication, a quantity of an ingredient in a unit of a medication, a mass of a unit of a medication, or a composition of a unit of a medication is within at least 65%, 70%, 75%, 80%, 85%, 90%, 95%, 99% or greater than 99% of an ingredient in a reference, a quantity of an ingredient in a reference, a mass of a reference, or a composition of a reference.

In some embodiments, a reference is a validated sample or the results of an analysis of a validated sample. In some embodiments, a validated sample was validated by a method descried herein. In some embodiments, a validated sample or batch is provided by a drug manufacturer, a pharmacy, a medical profession, a government agency, an end user, an entity or any source. In some embodiment, a reference conforms to a governmental standard. In some embodiments, a reference is for human consumption and provides a therapeutic benefit.

Medication Distribution

FIG. 4 illustrates an exemplary medication distribution model, in accordance with embodiments. In a standard medication distribution model, a drug distributor may distribute batches or subsets of a batches of unknown and untested quality and consistency to a pharmacy, which may in turn distribute medications of unknown and untested quality and consistency to patients. In a validated medication distribution model, a drug distributor may distribute batches or subsets of a batches of unknown and untested quality and consistency to a validation lab, which may in turn select batches or subsets of a batches and lots for testing and validation for quality and/or consistency. Bad batches or subsets of a batches of medications (which have failed quality and/or consistency standards or criteria) may be returned back to the drug distributor. Alternatively, subpar batches of validated medications may be sold to a reverse distributor. Quality batches or subsets of a batches of validated medications may then be sold by a pharmacy, or distributing business, which may in turn provide quality medications to the patient.

Computer Systems

Figure 5:
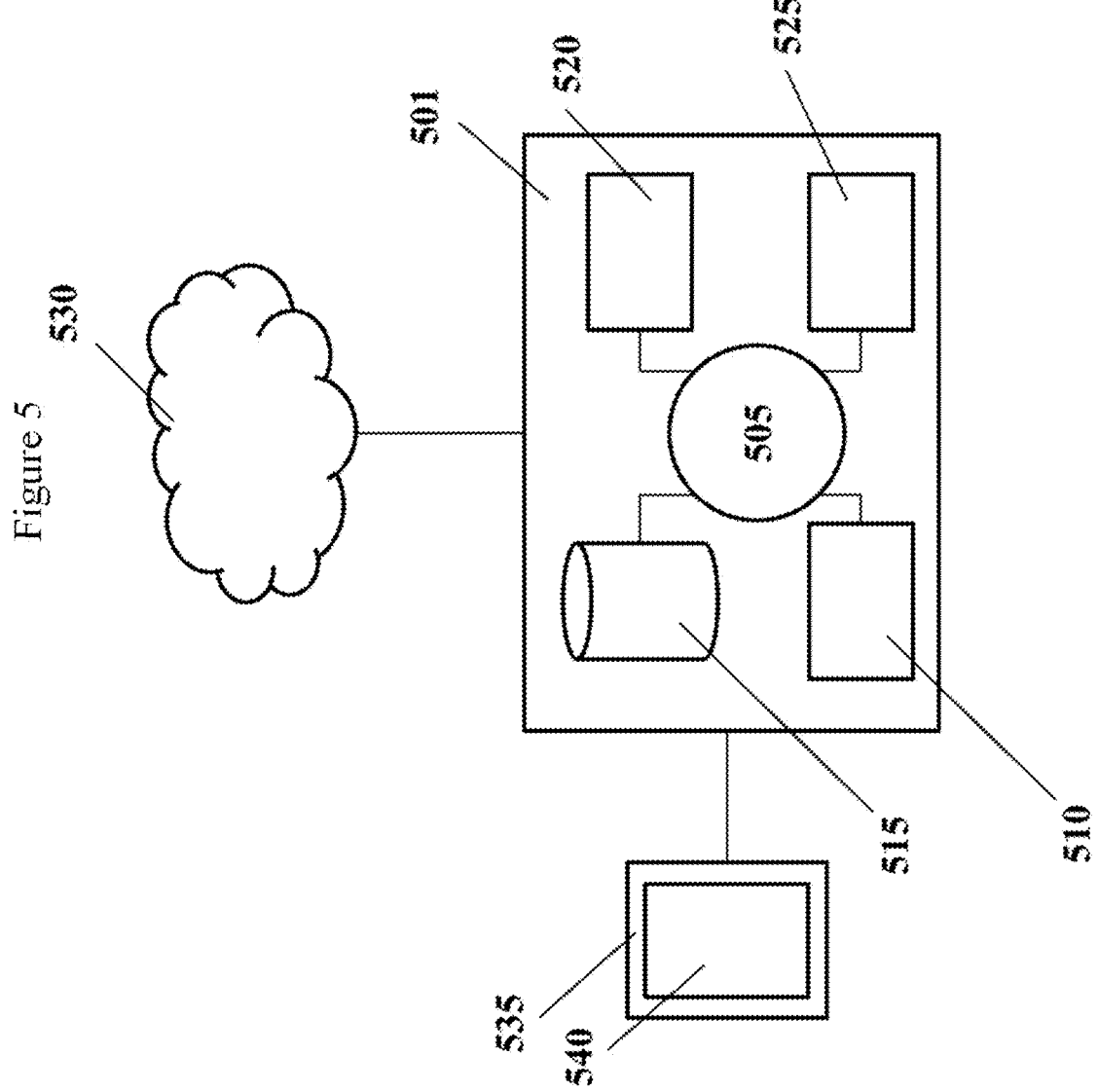
FIG. 5 shows a computer system 501 that is programmed or otherwise configured to implement methods provided herein.

FIG. 5 shows a computer system 501 that is programmed or otherwise configured to implement methods provided herein.

The computer system 501 can regulate various aspects of the present disclosure, such as, for example, analyzing an ingredient of a medication using an analytical test, and comparing the ingredient to a reference or derivative thereof. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, analyze an ingredient of a medication using an analytical test, and compare the ingredient to a reference or derivative thereof. In some cases a reference can be a manufacturer provided reference.

Examples

The following examples are given for the purpose of merely providing examples to illustrate various embodiments of the present disclosure, are not intended to limit the present disclosure in any fashion. The present examples, along with the methods described herein, are exemplary, and are not intended as limitations on the scope of the invention. Changes therein and other uses which are encompassed within the spirit of the invention as defined by the scope of the claims will occur to those skilled in the art.

In some aspects, if a drug-batch fails validation analysis based on statutory or regulatory standards, such a drug batch is also expected to fail a higher-quality (e.g., exceeding statutory or regulatory standards) medication standards. However, a batch that fails by a more stringent high-quality medication standard may still pass statutory or regulatory standards. If a drug-batch fails to pass even statutory or regulatory standards set forth by the appropriate regulatory agency in a jurisdiction, then it is deemed legally unfit for human consumption and is marked for return to the manufacturer. In some cases the failed drug/batch can be returned to a manufactured for a full refund, or is reported to the proper agency and/or is destroyed by the supplier. Alternatively, the supplier may return the failed batch to the manufacturer, and the manufacturer may destroy the failed batch.

Dissolution and Disintegration Analysis

Some dissolution protocols (for certain drugs) defined by private and/or government regulatory agencies are not well-grounded in scientific research. Higher-quality medication standards use scientifically developed protocols, such as a pH chosen for the dissolution medium that is representative of physiological gastrointestinal conditions.

A disintegration test (as per higher-quality protocol and standards) may be performed on a selected drug batch. If the batch fails by the higher-quality medication standards, then the batch will be marked accordingly, and the higher-quality pharmacy will not dispense it to an end-user. However, if batch fails by higher-quality medication standards, the analytical test is repeated on the same drug batch using protocol and standards set forth by a regulatory authority in the jurisdiction. If the batch also fails the regulatory authority's standards, then the failed batch is returned and reported for refund and destruction.

A dissolution test may be performed on a selected drug batch or subset of a batch. If the batch or subset of a batch fails by the higher-quality medication standards, then the batch or subset of a batch will be marked accordingly, and the pharmacy will not dispense it to an end-user or distributing business. Some dissolution protocols defined by regulatory agencies for certain drugs may not be well-grounded in scientific research. Higher-quality medication standards may incorporate scientifically developed protocols and standards for certain drugs to produce more stringent criteria for medication validation. For extended release drugs, the test may be performed to check that the release rate of the drug is consistent with label claim (e.g., by measuring an area under the curve of released drug).

Spectroscopic Analysis

Spectroscopic analysis of a medication may be performed by first preparing the medication and then performing spectroscopic analysis of the liquid or residual solids.

Preparation of the medication may comprise crushing a solid dosage-form, mixing the medication with a suitably chosen solvent, filtering the medication, and/or centrifuging the medication. All of the Active Pharmaceutical Ingredient (API) in the sample is dissolved in the liquid. In this process, due to careful choice of solvent, little else of the listed ingredients is dissolved. The residual solids comprise everything in the pill except the API and possibly unexpected/ unlisted impurities that dissolved in the solvent.

Spectroscopic analysis of liquid may be performed as follows. A scan of the empty tube (e.g., of the Raman spectroscopy machine) (without the liquid) is performed to obtain a background spectrum. Next, the prepared sample is loaded into a tube holder of the spectroscopy machine. Next, a full-tube scan (with the liquid loaded in the tube) is performed to obtain the spectrum consisting of a sum of the sample, solvent, and background spectra. The background spectrum is then subtracted off to obtain a clean signal (sample and solvent spectrum) for analysis.

The sample and solvent clean spectrum is compared to a reference or template spectrum collected in the past for that API and solvent combination. Kernel-smoothed first-derivative zeros are used for a first-pass check on peak locations to verify API identity. Any anomalous spectral features can be indicative that some impurity is detected. An explicit check for spectral activity, comprising a zeroth-order derivative with no kernel smoothing, is performed at locations corresponding to peaks of impurities known to be of concern for the specific drug, and/or highly toxic impurities. This explicit, focused check allows for a better limit-of-detection.

Next, in some embodiments, a quantitation algorithm may be applied, which has been previously calibrated for the particular API and solvent combination, on the sample and solvent clean spectrum. An outer-product is calculated of the spectrum (treated as a vector) and the element-wise multiplicative inverse of the spectrum. A set of API concentration estimates is generated using calibration parameters and many triplets of points from pre-optimized locations in the outer-product-ratio matrix. A calibrated estimator is applied to aggregate concentration estimates. Bootstrap methods are used with the aggregate estimator and resampled sets of concentration estimates to obtain a non-parametric confidence interval. The solvent mass, pill mass, etc. are used in conjunction with the final output to generate a confidence interval for the total API content in the analyzed pill. Fluorescence corrections may be performed using standard methods, as needed.

Spectroscopic analysis of residual solids may be performed as follows in some embodiments. The same scanning methods as for spectroscopic analysis of liquids are applied. The list of inactive ingredients that are supposed to be in the particular pill (e.g., a particular product's national drug code (NDC)) being analyzed is retrieved from a database of active and inactive ingredients stored for each particular medication. The spectra for each of these inactive ingredients is retrieved from a spectral library (which can be generated by performing spectroscopic analysis of known ingredients) and subjected to closer scrutiny and analysis. The spectral library may contain spectra corresponding to sets of one or more inactive ingredients for each of a plurality of different medications (e.g., each for a given formulation and dose from a given manufacturer). Such sets of one or more inactive ingredients for each of a plurality of different medications can be obtained from publicly available databases, such as those maintained by the U.S. Food and Drug Administration (FDA). The spectral library for such sets of inactive ingredients for different medications may be stored in a local database for ease and speed of retrieval. For example, the spectral library for such sets of inactive ingredients for different medications may comprise about 10, about 20, about 30, about 40, about 50, about 100, about 150, about 200, about 250, about 300, or more than 300 different inactive ingredients. Such a spectral library may span the set of possible inactive ingredients for a significant majority (e.g., at least 70%, at least 80%, at least 90%, at least 95%, or at least 99%) of all FDA-approved drugs. By restricting computational analysis to a narrowed or reduced set of spectra (e.g., Raman spectra) corresponding to a known list of one or more inactive ingredients to be analyzed, quantified, and/or verified for a particular medication, the testing process can be performed with significantly higher performance (e.g., speed, accuracy, and/or efficiency) . For example, the narrowed or reduced set of spectra may correspond to a known list of 1, 2, 3, 4, 5, 6, 7, 8, 9, 10, 15, 20, or more inactive ingredients for the medication.

Next, every feature observed in the sample spectrum to be verified may be associated with some inactive ingredient that is supposed to be in the pill. In other words, a check is performed to ensure that no unknown ingredient that is not listed as appearing in the pill is observed in the spectral analysis. For each inactive ingredient in the known list of one or more inactive ingredients for a given medication, the analysis may indicate whether or not that inactive ingredient is detected in the medication. Optionally, the analysis may also indicate a detected quantity of the inactive ingredients in the medication.

Next, in some embodiments, algorithms are performed for identification and approximate quantitation of inactive ingredients, with particular restriction to the spectral library generated from the retrieved short list which is specific to that drug's national drug code (NDC). These algorithms may comprise standard Raman spectroscopic analysis (e.g., quantitative or semi-quantitative), with some modifications. First, the solvent system is used to separately analyze the API, thereby obtaining an extremely precise quantitative measurement of API content and better limits of detection (LODs) for impurities or contaminants that are related to the API being analyzed (e.g., bupropion impurity A). For example, the LOD of impurities or contaminants may be about 0.1%, about 0.2%, about 0.5%, about 1%, about 2%, about 3%, about 4%, about 5%, about 6%, about 7%, about 8%, about 9%, about 10%, about 20%, about 30%, about 40%, about 50%, or more than 50% of the API weight. The off-the-shelf Raman analysis is performed on the leftover, non-API components of the pill or a separate, homogenized sample of the pill. Second, because an exact list of ingredients that a particular pill is expected to contain is known from the national drug code (NDC) for the pill, an exact list of substances the pill should contain can be retrieved from the database. Thus, a routine identification algorithm can be performed with a narrowly tailored spectral library. If the pill contains any substance or impurity not found on this list of substances, the batch or subset of a batch could be failed and not dispensed. By concentrating analysis on detection of any unknown substances, the special structure of the experimental circumstances can be exploited and external information can be leveraged to better produce a correct answer. In addition, semi-quantitative analysis may be performed (rather than more thorough quantitative analysis) to produce a rough approximation (e.g., with no more than about 10%, about 20%, about 30%, about 40%, or about 50% error) of quantitation of inactive ingredients.

Certificate of Analysis (CoA) Information Included With Dispensed Medications

One or more of the following certificate of analysis (CoA) information may be included with dispensed medications: API identity confirmation, API dosage confirmation with a confidence interval (e.g., "±10%", "±9%", "±8%", "±7%", "±6%", "±5%", "±4%", "±3%", "±2%", "±1%", "±0.5%", "±0.2%", "±0.1%"), Major inactive ingredients, Disintegration test passage confirmation, Dissolution test passage confirmation, and bound(s) on dissolution time (e.g., "<2 hr", "<60 min", "<45 min", "<30 min", "<20 min", "<15 min", "<10 min", "<5 min", "<3 min", "<2 min", and "<1 min"; or ">45 min", ">90 min", ">180 min," etc.).

In addition, additional certificate of analysis (CoA) information may be included with dispensed medications. For example, CoA information may indicate the medication's stability and expiration date confirmation. A particular batch or subset of a batch of medication may be tested at each of a plurality of time points over duration of time to confirm the stability of the drug. As another example, CoA information may indicate the medication's detected impurities (e.g., any heavy metals, cyanide groups, or other substances with potential toxicity concerns). Heavy metals may be detected using suitable detection techniques such as X-ray fluorescence. Such impurities may comprise isomers or enantiomers of APIs. For some drugs (e.g., bupropion) known drug-specific impurities may be targeted for detection. As another example, CoA information may indicate the medication's detected allergens, such that end-users having allergies to such allergens may be made aware of a contraindication of use.

For certain drugs and/or dosage forms, the analytical techniques as outlined above may not be appropriate. For example, dissolution testing is generally not appropriate for liquid dosage forms (e.g., eye-drops). As another example, spectroscopy analysis may not be suitable for quantitation of some ultra-low-dosage drugs (e.g., oral ethinylestradiol/levonorgestrel formulations). In such cases, alternative assay methods, such as ultra-high performance liquid chromatography (UHPLC) and/or nuclear magnetic resonance (NMR) spectroscopy, may be employed. A still-higher-quality screening process to ensure penultimate quality may be optionally enhanced using custom-designed analytical technology such as hardware. However, such custom-designed analytical technologies are not necessary for higher-quality screening, nor is the scope of the process necessarily restricted to the specific analyses described above. Quality validation assessments may include, for example, validation of one or more basic quality and/or consistency properties (e.g., whether a dosage unit contains the API as indicated on the label and in the correct amount, whether the API is being released at the correct rate, whether the dosage unit contains any substances that are not indicated on the label), but additional quality-validation assessments may be incorporated.

In some embodiments, a summary of analytical results is provided in the form of a certificate of analysis (CoA) as one part of the medication validation process. The medication screening (e.g., rejecting, and not distributing, batches or subsets of a batches of medications that fail to meet higher-quality medication standards) is a significant component of the process. The CoA provides concrete documentation, traceability, accountability, and reassurance that the medication validation testing has been performed. However, end-users or distributing businesses do not have a need to act on such information, because their higher-quality medication distributor (e.g., online pharmacy or distributing business) will preemptively take the required actions (removal and replacement of batches or subsets of a batch that fail the higher-quality medication validation tests) before distributing to end-users or distributing businesses.

By providing the summary of analytical results in the form of a certificate of analysis (CoA), the end-user or distributing business is assured that the medications have been quality checked at the penultimate location before dispensing. Such quality assurance may be especially important for medications that have been supplied through a de-centralized supply chain. Higher-quality medication validation may also ensure consistency of medications dispensed to an end-user or distributing business over time, even if there are drug shortages (e.g., from a certain manufacturer due to scarcity of raw materials). In contrast, performing validation of medication quality by simply checking quality-control (QC) or quality-assurance (QA) barcodes may disadvantageously place undue reliance and trust on every entity in the complex supply chain that produced the medication, including raw material producers, distributors, warehouses, pharmacies, and resellers, who may be located in many different countries.

Although the description has been described with respect to particular embodiments thereof, these particular embodiments are merely illustrative, and not restrictive. Concepts illustrated in the examples may be applied to other examples and implementations.

While preferred embodiments of the present invention have been shown and described herein, it will be obvious to those skilled in the art that such embodiments are provided by way of example only. It is not intended that the invention be limited by the specific examples provided within the specification.

While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for validating a plurality of medication batches post-manufacturing, the method comprising:

(a) obtaining at least one sample from the plurality of medication batches post-manufacturing, wherein each medication batch post-manufacturing of the plurality of medication batches post-manufacturing comprises a same active ingredient from the same manufacturer;

(b) performing an analytical test on the at least one sample from the plurality of medication batches post-manufacturing to determine one or more analysis result;

(c) determining a validation status of the plurality of medication batches post-manufacturing based on at least one of the one or more analysis result; and (d) providing an indication of the validation status of the plurality of medication batches post-manufacturing to a drug manufacturer, a distributor, a pharmacy, a medical professional, a government agency, or an end user.

2. The method of claim 1, wherein the analytical test comprises at least one analytical test selected from the group consisting of: nuclear magnetic resonance spectroscopy, mass spectrometry, high-performance liquid chromatography, Fourier transform infrared spectroscopy, and Raman spectroscopy.

3. The method of claim 1, wherein the indication of the validation status is provided on a report.

4. The method of claim 3, wherein the report comprises an indication of one or more of: analytical tests performed on the at least one sample from the plurality of medication batches post-manufacturing, a number of ingredients analyzed, adherence to a quality standard, deviation from a reference quantity, dissolution test results, or any combination thereof.

5. The method of claim 3, wherein the report comprises an indication of indicates one or more-impurities present in the at least one sample from the plurality of medication batches post-manufacturing.

6. The method of claim 1, wherein the at least one sample from the plurality of medication batches post-manufacturing is in a solid form selected from the group consisting of: a pill, a capsule, a tablet, and a powder.

7. The method of claim 1, wherein the at least one sample from the plurality of medication batches post-manufacturing is in a non-solid form selected from the group consisting of: a liquid, a cream, a lotion, a paste, and a gel.

8. The method of claim 1, wherein the at least one sample from the plurality of medication batches post-manufacturing is a sample selected from the group consisting of: a drug prescribed by a licensed healthcare practitioner, a drug purchased over-the-counter, a drug purchased over the internet, a drug acquired from a manufacturer, and a drug acquired from a distributor.

9. The method of claim 1, wherein the at least one sample from the plurality of medication batches post-manufacturing is taken from a container or package containing more than one unit of a medication batch of the plurality of medication batches post-manufacturing.

10. The method of claim 1, wherein the at least one sample from the plurality of medication batches post-manufacturing comprises a biologic, a pharmaceutical, a veterinary drug, or any combination thereof.

11. The method of claim 1, wherein performing the analytical test of (b) comprises techniques for identifying chemicals, techniques for verifying the integrity of pharmaceutical products, or both.

\* \* \* \* \*